Figure 1:
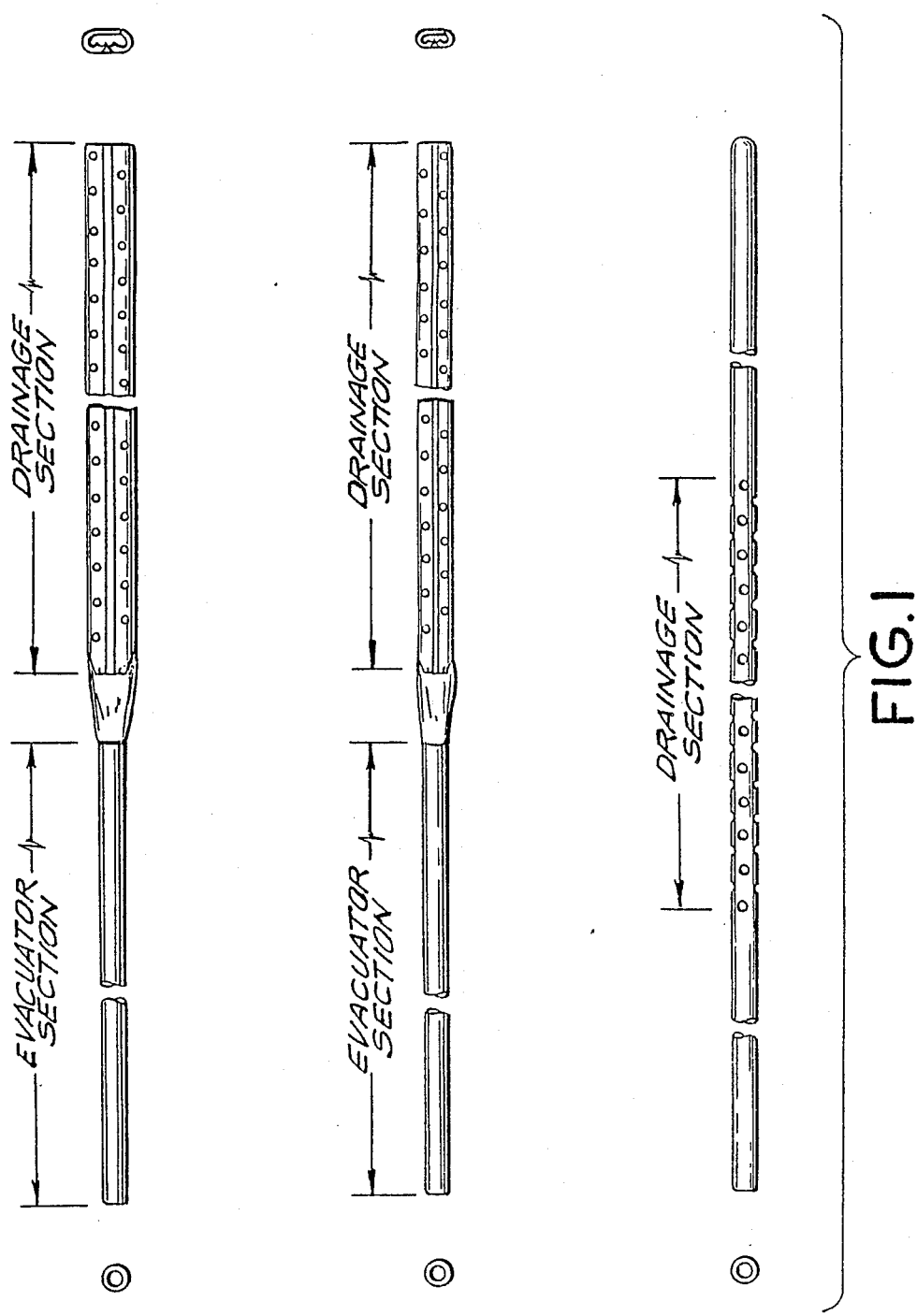

United States Patent [19]

Baker et al.

[11] Patent Number: 4,980,231
[45] Date of Patent: Dec. 25, 1990

[54] PROCESS FOR COATING POLYMER SURFACES AND COATED PRODUCTS PRODUCED USING SUCH PROCESS

[75] Inventors: John H. Baker, Strasburg; Kim R. Harmon, Mineral City, both of Ohio

[73] Assignee: Snyder Laboratories, Inc., Dover, Ohio

[21] Appl. No.: 308,678

[22] Filed: Feb. 13, 1989

Related U.S. Application Data

[63] Continuation-in-part of Ser. No. 157,892, Feb. 19, 1988, abandoned.

[51] Int. Cl.⁵ .............................................. B29D 27/00
[52] U.S. Cl. ................................ 428/36.9; 428/423.1; 428/447; 428/451; 428/483; 428/522; 427/393.5; 523/112; 524/267; 524/266; 525/102; 604/265

[58] Field of Search ............... 524/267, 266; 525/102; 427/393.5; 523/112; 604/265; 428/451, 447, 522, 36.9, 483, 423.1

[56] References Cited

U.S. PATENT DOCUMENTS

| | | | |
|---|---|---|---|
| 3,925,178 | 1/1976 | | 204/165 |
| 4,100,309 | 9/1978 | | 428/234 |
| 4,119,094 | 10/1978 | Micklus | 128/132 R |
| 4,312,575 | 1/1982 | Peyman | 351/160 |
| 4,589,879 | 5/1986 | Pearson | 604/411 |

Primary Examiner—Edith Buffalow
Attorney, Agent, or Firm—Helfgott & Karas

[57] ABSTRACT

Processes for treating polymeric surfaces to produce smooth, durable, slippery coatings which are able to withstand the rigors of sterilization and, long term exposure to human blood and other bodily fluids without substantial loss of their slipperiness. An article or device suitable as a wound drainage device coated in accordance with the process described is also disclosed.

23 Claims, 18 Drawing Sheets

PROCESS FOR COATING POLYMER SURFACES AND COATED PRODUCTS PRODUCED USING SUCH PROCESS

FIELD OF THE INVENTION

This invention, a continuation in part of U.S. Ser. No. 07/157,892, filed Feb. 19, 1988 now abandoned, relates to the field of coatings for polymer surfaces and particularly to processes for treating polymeric surfaces to produce smooth, durable, slippery coatings which are able to withstand the rigors of sterilization and long term exposure to human blood and other body fluids without substantial loss of their slipperiness. More particularly this invention relates to a process for coating surgical devices made of various polymeric materials to provide a superior smooth, durable slippery coating thereon.

BACKGROUND OF THE INVENTION

The use of devices made from various polymeric materials, including silicone rubber and polyvinyl chloride (PVC) and the like, has achieved an important place in carrying out numerous surgical procedures. An important class of such devices consists of various wound drainage devices, surgical inserts and surgical tubing all of which are important in the removal of blood and other fluids from a surgical or wound site.

Generally speaking in the course of such procedures a tubular device made of some inert, usually polymeric material, must be inserted and positioned through body tissue and must allow unrestricted flow of blood through the device for up to several days. The presently available devices, especially those made of silicone, have undesirably high resistance to movement through tissue. A greater problem is an undesirably high level of blood clot formation inside drainage tubes, especially those made from silicone and PVC. Most serious of all, the clots which form, especially in silicone, are difficult to remove. These undesirable characteristics primarily derive from the fact that silicone rubber tubing has a very hydrophobic surface which is very poorly wetted by aqueous media. Devices made from PVC, although better performing than silicone, also have poorly wetted, nonslippery surfaces.

Thus it has been deemed desirable to develop a process which would allow one to coat the surfaces of devices made from various polymeric materials, such as for example silicone, PVC, latex, polyester, polyurethane, and thermoplastic elastomers, to improve the wettability and slipperiness of such devices, particularly under conditions encountered when such devices are employed in wound drainage applications.

Amongst the prior art in which the applicants are aware dealing with the problem of coating various polymeric materials in contact with human body fluids are the following:

U.S. Pat. No. 4,100,309 discloses a multistep method of applying a hydrophilic coating on a substrate.

U.S. Pat. No. 4,119,094 is related to U.S. Pat. No. 4,100,309 and claims articles coated in accordance with the process set out therein.

U.S. Pat. No. 3,925,178 discloses a process for treating a plastic contact lens to make the lens surface hydrophilic without changing the optical characteristics of the lens.

U.S. Pat. No. 4,312,575, also discloses contact lenses having an ultrathin, clear, lipid-permeable hydrophilic barrier coating which is formed by an electrical glow discharge process.

U.S. Pat. No. 4,589,879 teaches a method for coating vinyl tubing with PVP using DMF as a solvent. The coated product produced is however found to be distorted and the coating uneven and of very poor quality.

None of the foregoing references teaches the process or the products produced thereby which are the subject of the present invention.

SUMMARY OF THE INVENTION

The present invention is directed to a process for treating polymeric surfaces to produce smooth durable slippery coatings which are particularly suited for use as wound drainage or other surgical devices. Products made from such coated polymeric materials are also taught herein.

DESCRIPTION OF THE INVENTION

It has been found that producing a hydrogel surface on a silicone, PVC, latex, polyester, polyurethane, or thermoplastic elastomer surface, that is, one which is wettable and slippery in water, will substantially improve the performance of wound drainage devices constructed from silicone rubber and PVC. For example, the frictional forces produced on the surfaces of such devices by inserting or removing them through tissue will be greatly reduced. More importantly the tendency for the blood to clot has been shown to be lessened and the ease of clot removal is greatly enhanced by such a coated surface. It is generally recognized that a fluorinated surface (i.e. Teflon or Teflon-like) is much less prone to blood clot formation (i.e. is less thrombogenic) than a silicone rubber or PVC surface, probably because it has a lower energy surface, and a lower coefficient of friction. Hence, low energy fluorinated surfaces are also expected to produce surfaces with lesser blood clotting tendencies and less adherence of blood clots if they do form.

The object of the present invention is a process or treatment which will provide improved surface properties to wound or surgical drainage devices made from various polymeric materials, including silicone, PVC, latex, polyester, polyurethane and thermoplastic elastomers. The improved surface properties to be achieved will consist of either a more wettable, slippery surface, or a lower energy, less thrombogenic surface. These characteristics are to be provided, respectively, via physically or chemically anchored hydrogel polymer coatings, or by a fluorinated or polyfluorocarbon coated silicone rubber and PVC surface. The modified polymeric surface must meet four conditions or criteria to be successful.

The criteria, or specifications, for an acceptably treated (coated) wound drainage device are the following:

1. The modified surface must retain this characteristic for a minimum of 100 hours when in contact with wound secretions.

2. The process and/or condition which produces such a surface must be applicable to the inside and outside diameters of round tubes and irregular cross-sectional shaped tubes. These round tubes and/or combinations of irregular shapes are known as closed wound drainage devices, usually used in combination with a suction device; such as Snyder Hemovac ™ or Surgivac ™.

3. The modified surface must be able to withstand an ethylene oxide sterilization process and not deteriorate, crack, have an adversely affected shelf-life, or impair the physical characteristics or properties of the polymeric substrate layer or surface.

4. The process and/or condition which produces such a surface must be safe (e.g., FDA approvable, pass USP XIX class IV), reasonable and feasible to scale-up in a continuous, semi-continuous or batch manufacturing mode.

It should be understood that there are significant differences for example between silicone rubber (cross-linked polydimethysiloxane) and flexible vinyl (PVC). The basic polymer structures are as follows:

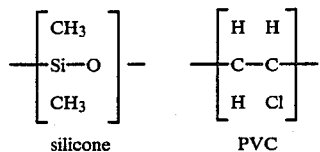

However, the silicone as used is a filled (silica), cross-linked (i.e., three dimensional, insoluble network) rubber, while the PVC is a soluble thermoplastic containing a solvent leachable plasticizer and no filler. The silicone is a relatively stable, low surface energy (highly nonwater-wettable) material while PVC has an intermediate surface energy and water wettability and is relatively susceptible to reaction due to the chlorine-carbon bonds (loss of HCL via heat or strong base, possible quarternization with amines). However, the silicone has some residual chemically reactive silane (SiH) and/or vinyl ($SiCH—CH_2$) groups. These were the groups used to cure (cross-link) the rubber. They are potentially usable for chemical attachment (grafting), if they are present in sufficient concentration, on or near the tubing surface. The silica filler in the silicone also possesses reactive surface silanol (SiOH) groups usable for grafting, again if a sufficient concentration of these groups is at or just below the rubber surface, to provide a useful degree of bonding.

A complication with PVC is the presence of the organic ester (e.g. dioctyl phthalate) plasticizer, which can both migrate (bloom) to the surface and interfere with surface reactions, or be leached out during solution or solvent treatment, resulting in a hardened, perhaps more brittle or crack-prone surface.

However, it must be remembered that vinyl tubing is not cross-linked and any organic liquid which is a solvent for PVC will attack or erode the tubing. This is in contrast to the silicone tubing, which is cross-linked and swells but cannot dissolve in a liquid which is a solvent for uncross-linked silicone. Hence silicone rubber can be easily and conveniently impregnated with a number of potential coupling or grafting agents, using a range of solvents and soaking conditions, while solvent solutions for treating vinyl must be chosen and used with care.

Hence, although some coating or treating methods can be used on both silicone, PVC and other polymeric materials, the special requirements of the substrates' surfaces must be kept in mind and the procedures adapted to the surfaces as required; some possible treatment procedures will be unique to the particular surface utilized.

A chemical process has been developed for coating drainage tubes with a hydrophilic polymer that substantially reduces the coefficient of friction and surface tension of these drain materials. The coating provides an extremely soft, slippery outer surface which enhances ease of installation and removal, while minimizing frictional irritation of surrounding cells and tissue. The internal coating provides a surface with a low interfacial tension substantially reducing intraluminal and fenestration port adhesion of blood, blood clots, or other exudate, thus decreasing the negative pressure required to evacuate the wound and increasing the rate of flow through the drain.

The coating process of the present invention provides a chemical bond between the polymeric drain materials and a polyvinylpyrrolidone hydrogel, treated with a silane and copolymer to provide a highly biocompatible coating while maintaining clarity, radiopacity, and other physical properties of the drains.

The coating material is a hydrogel. A hydrogel is a polymeric material which exhibits the ability to swell in water and retain a significant fraction (e.g., 20%) of water within its structure, but which will not dissolve in water. Hydrogels have been shown to have great potential as blood and tissue compatible materials.

In theory, hydrogels are attractive as biomaterials because they are similar to the body's own highly hydrated composition. Thus, if the interface of a foreign object does not appear foreign to the biomolecules and cells in the vicinity, then they should not be attracted to the interface.

In keeping with the foregoing considerations a treatment procedure has been developed that gives a more slippery surface than untreated controls for various polymeric materials which comprises the following general steps:

In the case of a silicone, latex, polyester, polyurethane or thermoplastic elastomer polymeric surfaces:

Application of a tie coat comprising a solution of a poly(methyl vinyl ether/maleic anhydride) such as AN 119, AN 139, AN 149, Gantrez AN-169 or AN-179 (GAF Corp.) in a 1:1 methanol/isopropanol; followed by a heat-dry cycle, then, Application of a slippery coating comprising a combined solution of polyvinyl pyrrolidone (PVP), K-90 (GAF Corp.) and N-trimethoxypropyl silyl polyethylenimine (PSO76-Petrarch) in isopropanol; followed by a further heat dry cycle.

In the case of a polyvinylchloride polymeric surface:

Application of a slippery coating comprising a combined solution of polyvinyl pyrrolidone (PVP), K-90 (GAF Corp.) and N-trimethoxypropyl silyl polyethylenimine (PSO76-Petrarch) in n-propyl alcohol, followed by a heat dry cycle in an air-circulating oven at 80° C. for about 20 minutes.

Generally, for silicone polymer applications the article will first be treated with 1:1 solution of methanol and isopropanol containing from about 0.25–4.0 wt. % of a polymethyl-vinyl ether/maleic anhydride, such Gantrez as AN-169 (GAF Corp.) or the like. Preferably about 1 wt % Gantrez AN-169 in a methanol/isopropanol solution will be used. However, any solvent can be utilized with equal effect, which solubilizes the Grantez and permits it to adhere to the surface of the silicone.

It has been found that a 50/50 methanol/isopropanol (IPA) mixture swells the silicone rubber two to three times as much as methanol alone, while isopropanol swells it even more. The degree of swell in the priming step for treating silicone is very important in obtaining the durable, slippery when wet, coating of PVP/PSO76. The Gantrez AN169 half ester is probably impregnated into the silicone surface if the degree of swelling is −1.5 percent. Consequently isopropanol alone is expected to work especially well as the Gantrez impregnating solvent.

In any event these swelling data, see Table 1, strongly suggest that some degree of swelling is needed to achieve a good result from the two step coating procedure on silicone.

TABLE 1

SWELLING OF SILICONE TUBING IN LOWER ALCOHOLS AND ALCOHOL MIXTURES[a]

| Alcohol | Weight Gain (Percent by Weight) Versus Swelling Time in Minutes | | | | | |
|---|---|---|---|---|---|---|
| | 10 | 20 | 60 | 180 | 360 | 4320 |
| Methanol[b] | 1.2 | 1.4 | 1.5 | 1.2 | 0.9 | 0.7 |
| Ethanol[c] | 2.1 | 3.2 | 4.3 | 4.8 | 4.6 | 4.1 |
| n-Propanol[d] | 3.9 | 5.4 | 7.7 | 12.78 | — | 14.6 |
| n-Butanol[e] | 4.6 | 6.7 | 11.4 | 15.7 | 17.5 | 17.9 |
| n-Pentanol[f] | 4.3 | 6.1 | 9.0 | 13.0 | 13.8 | 14.3 |
| iso-Propanol[g] | 5.6 | 8.0 | 13.5 | 19.3 | 21.6 | 22.1 |
| 1/1 Methanol/ n-Propanol[h] | 2.3 | 2.8 | 3.9 | 4.3 | — | 3.5 |
| 1/1 Methanol/ iso-Propanol[h] | 2.1 | 2.6 | 3.9 | 4.2 | — | 3.3 |

[a]High chemical purity, well dried alcohols used at room temperature (70 F., 23 C.). All swelling experiments in run triplicate and weight gain results averaged.
[b]Burdick and Jackson distilled in glass, <0.05 percent water.
[c]Absolute ethanol, dried over mol sieve 3A.
[d]Aldrich Gold Label (<0.005 percent water).
[e]J. T. Baker Reagent grade (<0.05 percent water).
[f]n-Pentanol, Metheson Coleman and Bell, 99+ mole percent pure.
[g]J. T. Baker reagent grade, dried over mol sieve 3A.
[h]50/50 mixture by volume.

Based upon evaluations undertaken it has been determined that methanol alone is not nearly as effective a solvent for treatment of silicone as the 50/50 methanol/isopropanol blend or IPA alone. This appears to be a function of degree of swelling.

Similar results are obtained with vinyl (PVC) tubing where only isopropanol (IPA) is used as solvent, except that some wettability is noted when methanol alone is used as the coating solvent. However, the use of the mixed alcohols or IPA alone as the solvent results in definitely better slipperiness. Also it is quite clear that PSO76 must be used along with the PVP or the highly slippery wettability is lost much more quickly and readily.

It is believed that there is a substantial and important difference in the final slipperiness and its durability between the use of methanol alone and of 50/50 methanol/IPA or IPA alone as the solvents, on both the silicone and vinyl substrates that is not anticipated in the prior art.

The heat-dry cycle following the initial treatment with the Gantrez solution is accomplished by placing the treated article in an air-circulating oven at 80° C. for about 15 minutes.

The second step in the treatment process of the present invention for silicone polymer latex, polyester, polyurethane or thermoplastic elastomers involves the application of a combined solution of PVP and PSO76, followed by a heat-dry cycle to form a slippery coating.

Generally speaking for silicone polymer products this solution will be a solution containing from about 0.25 to about 5.0 weight percent PVP and from about 0.1 to about 1.0 weight percent PSO76 in pure isopropanol.

Preferably, a solution containing about 2 wt. percent PVP and about 0.2 wt percent PSO76 will be utilized in pure isopropanol.

Generally speaking, for polyvinyl chloride polymeric products the combined solution of PVP and PSO76 will be applied to the article directly without any pretreatment. The solution will generally contain from about 0.25 to about 5.0 weight percent of PVP and from about 0.1 to about 1.0 weight percent of PSO76 in pure isopropanol or n-propyl alcohol. Preferentially, about 2 weight percent PVP and about 0.2 weight percent PSO76 will be utilized in pure n-propyl alcohol.

Polyvinyl chloride (PVC) tubing has been dried in ovens (circulating air) set at 150° C., 200° C. and 250° C. Both untreated vinyl and tubing freshly treated with IPA were tested. At 150° C. the tubing withstands about 5 minutes before showing substantial evidence of softening and can be dried. However, at 200° C. all samples began to melt within 10–15 seconds and at 250° C. they melted almost immediately (5 seconds). It was impossible to dry vinyl tubing at these temperatures which are taught by the prior art.

A number of materials similar to PSO76 have been found to work with equal advantage. PSO76 alternates are listed in Table 2. These include PSO76.5, a closely related polymeric silane coupling agent and a number of other polymeric silane coupling agents. These are unique materials introduced by Petrarch. They are polymers with silane coupling functionality [—Si(OR)$_3$], where R is methyl or ethyl groups, attached as pendent groups on the backbone. There are also a number of the usual low molecular weight silane coupling agents used in industry for a number of years. These are made commercially by Dow Corning, Union Carbide and others. Lists of these products are appended. All coupling agents can self react, after hydrolysis (e.g., via moisture in air or condensed on a surface or added to a treatment procedure), through the intermediate [—Si(OH)$_3$] groups which form, or can form. Water is eliminated and siloxane (Si—O—Si) crosslinks form. These SiOH groups can also interact with organic hydorxyl groups resulting in Si—O—C crosslinks. Yet these coupling agent groups are thermally stable, and chemically stable in the absence of water. Hence they can be mixed with PVP, or other water or alcohol or organic solvent soluble polymers in dry alcohol or other dry organic solvent solutions without reacting. When the mixtures are exposed to water, as in coating procedures in air, and especially if a water treatment or wash is used, the chemical reaction described above leading to either (a) self-crosslinking of the silane coupling agent or (b) crosslinking of the silane coupling agent and the organic polymer (if some hydroxyl groups are available on the polymer), or (c) both, can occur. If these types of reactions occur, more durable, wettable coatings would be achieved—provided an appropriate balance of materials is maintained.

The polymeric coupling agents are, in general, actually shown to be much more active in producing gelled (i.e., crosslinked or cured) films (see Table 2) than the low molecular weight silane coupling agents. However, the quaternary salt coupling agents, with long aliphatic (fatty) groups attached also appear to be active. In addition, several other types of special polysiloxanes or silicone copolymers are shown to be potentially usable.

TABLE 2

PS076 ALTERNATES

| Item No. | Product Number | Chemical Type | Source | PVP Curing Agent[a] | Comments[b] |
|---|---|---|---|---|---|
| 1 | PS076 | (N-Trimethoxysilyl-propyl)polyethylene-imine | Petrarch Systems, Inc. | 3 | Ethyleneimine/silane coupling agent copolymer |
| 2 | A0700[c] | N-2-Aminoethyl-3-aminopropyl trimethoxysilane | Petrarch Systems, Inc. | 2 | Silane coupling agent amino functional |
| 3 | Corcat P-18 | Polyethyleneimine | Virginia Chemicals[d] | 2 | Polyethyleneimine |
| 4 | PS076.5[e] | (Dimethoxysilyl-propyl)polyethylene-imine | Petrarch Systems, Inc. | 3 | Ethyleneimine/silane coupling agent copolymer |
| 5 | PS075[j] | (N-Trimethoxysilyl propyl)polyazamide | Petrarch Systems, Inc. | 5 | Polyamide/silane coupling agent |
| 6 | PS078.5 | Triethyoxysilyl modified poly(1,2-butadiene) | Petrarch Systems, Inc. | 4 | Polybutadiene/silane coupling agent |
| 7 | PS074.2 | Methacrylate functional polymeric silane | Petrarch Systems, Inc. | 4 | Complex polymeric silane coupling agent copolymer[1] |
| 8 | PS072[g] | Dimethylsiloxane ethylene oxide-propylene oxide copolymer | Petrarch Systems, Inc. | 4 | Polysiloxane-hydrophilic organic block copolymer |
| 9 | PS922 | Glycidoxypropyl-methyl (45–55%) dimethylsiloxane copolymer | Petrarch Systems, Inc. | 5 | Epoxy-functional silicone copolymer |
| 10 | PS9120[h] | Polydiethoxysilane (40–42% SiO$_2$ content) | Petrarch Systems, Inc. | 5 | Polyorganosilicate precursor of poly-silicic acid and hydrophilic silica |
| 11 | PS077 | (N-Trimethoxysilyl-propyl)-O-poly-ethylene oxide urethane | Petrarch Systems, Inc. | 4 | Polyethyleneglycol urethane silane coupling agent |
| 12 | 09745 | Octadecyldimethyl [3-(Trimethoxysilyl)-propyl] ammonium chloride | Petrarch Systems, Inc. | 4 | Silane coupling agent quaternary ammonium salt[i] |
| 13 | T1803 | N-Tetradecyldimethyl (3-trimethoxysilyl-propyl) ammonium chloride | Petrarch Systems, Inc. | 4 | Silane coupling agent quaternary ammonium salt[i] |
| 14 | G6720[k] | (γ-Glycidoxypropyl) trimethyoxysilane | Petrarch Systems, Inc. | 3 | Silane coupling agent epoxy functional |
| 15 | T2924 | N-Trimethoxysilyl-propyltri-N-butyl ammonium bromide | Petrarch Systems, Inc. | 2 | Silane couplng agent quaternary ammonium salt |
| 16 | I7840 | Isocyanatopropyl-triethoxysilane (95%) | Petrarch Systems, Inc. | 3 | Silane coupling agent isocyanate functional |
| 17 | T2507 | N-(Triethoxysilyl-propyl) urea | Petrarch Systems, Inc. | 1 | Silane coupling agent urea functional |
| 18 | D4520 | Diethoxyphosphate-ethyl triethoxysilane | Petrarch Systems, Inc. | 1 | Silane coupling agent diethyl phosphate functional |
| 19 | Corfax 712 | Fatty alkyl substituted polyethylene- | Virginia Chemicals[d] | 1 | Dispersant/surfactant with reactive amines |

TABLE 2-continued
PS076 ALTERNATES

| Item No. | Product Number | Chemical Type | Source | PVP Curing Agent[a] | Comments[b] |
|---|---|---|---|---|---|
| | | imine | | | |

[a]Approximately 0.2–0.4 percent of the test material added to 1 gram of a 2.0 percent PVP (K90) solution in isopropanol in 4 dram glass vials and the solution or cloudy dispersion taken to dryness at 80 C. (~2–3 hours), cooled, and 5 ml distilled water added. The samples were inspected and gently swirled by hand over a 8-hour period. The behavior of the solid film was rated in one of five categories as follows:
1. Dissolved readily to a clear solution, over 1–2 hours
2. Dissolved slowly to a clear solution, over 2–4 hours
3. Formed a gel which swelled greatly, then slowly dispersed until it was difficult to see, over 2–4 hours
4. Formed a gel which swelled greatly, then slowly dispersed to a cloudy dispersion, over 2–4 hours
5. Formed slightly swollen gel which remained intact over 8 hours

[b]General description identifies whether the material is polymeric in nature.
[c]Equivalent to Dow Corning Z-6020 and Union Carbide UC 1120.
[d]Division of Celanese Corp. (formerly Cordova Chemical Company).
[e]Modified version of PS076, with two reactive methoxysilyl groups per coupling agent unit, instead of three as in PS076
[f]Discontinued product formerly available from Petrarch.
[g]Three related products from Petrarch were not tested but would be expected to be equivalent. These are PS071, PS073, PS073.5, all dimethylsiloxane-ethylene oxide copolymers.
[h]Three related products from Petrarch were not tested but would be expected to be equivalent. These are PS912X, PS9130 and PS9150. The first two are polydiethoxysiloxanes with potentially higher $SiO_2$ content. PS9150 also contains 7–9% of a titanoxane ($TiO_2$ precursor) group.
[i]Quaternary salt portion of coupling agent has a long, aliphatic group (hydrophobic group).
[j]Quaternary salt portion of coupling agent has only low molecular weight butyl groups.
[k]Equivalent to Dow Corning 2-6040 and Union Carbide A-187.
[l]Methyl methacrylate/γ-trimethoxypropylsilyl methacrylate/vinyl pyrrolidone, vinyl-β methacrylatomethylate copolymer.

A summary of the classes of materials with ratings of 3–5 in Table 2 is the following:
Polymeric silane coupling agents—item numbers 1, 4, 5, 6, 7, 11
Reactive polydialkoxysiloxanes—item 10 and three (3) footnoted variants
Silicone polymer with pendent reactive organic functional groups—item 9
Silicone polymer with a chemically attached (block copolymer) hydrophilic, or water soluble, organic polymer—item 8 and three (3) footnoted variants
Low molecular weight, or non-polymeric, silane coupling agents—items 13, 14 and 16.

All the products with a rating of 3 to 5, including PSO76 (3) are considered good candidates for use in the process of the present application. Ratings of 2 indicate weak activity. Ratings of 1 indicate essentially none is expected.

Various alternates to Gantrez AN169 have been evaluated, these are set out in Table 3.

TABLE 3
GANTREZ AN-169 ALTERNATES

| Item No. | Product Number | Chemical Type | Source | PVP Curing Agent[a] | Comments[b] |
|---|---|---|---|---|---|
| 1 | 18,805-0 | Ethylene/maleic anhydride copolymer | Aldrich Chemical Co. | 5 | About 50 mole percent maleic anhydride |
| 2 | 18,293-1 | Styrene/maleic anhydride copolymer | Aldrich Chemical Co. | 5 | About 50 mole percent maleic anhydride, 50,000 molecular weight |
| 3 | 18,128-5 | Polyacrylic acid | Aldrich Chemical Co. | 5 | Molecular weight 250,000 |
| 4 | 2348 | Polymaleic anhydride | Polysciences, Inc. | 5 | Homopolymer of maleic anhydride |
| 5 | 3347 | Poly(vinyl acetate-maleic anhydride) | Polysciences, Inc. | 4 | |

[a]Same as Table 2 Gantrez AN-169, also rates a 5.
[b]Same as Table 2

In addition to the Gantrez AN-169 alternate candidates tested in Table 3, others are also expected to work with equal advantage. These include any polymers or copolymers of acrylic or methacrylic acid, maleic anhydride, crotonic anhydride, or any other carboxyl-group-containing, or nascent carboxyl-group-containing (i.e., anhydride groups) polymers which are directly soluble in methanol, ethanol, n-propanol, isopropanol, or other lower alcohols, or which are soluble in these alcohols after hydrolysis to the free carboxyl-group-containing polymers. Polymers or copolymers with other strong acid groups such as sulfonic acid or phosphoric acid groups, which are similarly soluble, would also be expected to be usable.

Any organic solvents other than the silicone-swelling alcohols (see Table 1) ethanol through isopropanol, such as methylene chloride, 1,1,1-trichloroethane, MEK, methyl acetate and so on, which dissolves these polymers or copolymers, and swells silicone rubber to some extent are also candidates for use in silicone rubber treatments, using PVP, or a high vinyl pyrrolidone copolymer as the wettable, slippery coating polymer.

In addition to PVP K-90, lower molecular weight PVP products from GAF Corp. may be used in place of PVP-K90, although they are not expected to be as good in durability. Higher molecular weight polyvinyl pyrrolidone homopolymers if available, would be expected to perform better than PVP K-90. However, the ease of dissolution and the application ease of higher molecular weight products will be diminished as higher solution viscosities are encountered. Vinyl pyrrolidone copolymers, which contain about fifty mole percent or more vinyl pyrrolidone (VP) monomner are expected to show some of the beneficial properties of PVP K-90, if they are soluble in the same lower alcohols cited above and in Table 1 and can thus be coated on primed silicone (silicone primed with an alcohol solution of Gantrez AN-169 or other appropriate acid-group-containing polymer or copolymer). For example, GAF supplies vinyl acetate/vinyl pyrrolidone (e.g., E-735, 70/30 VAc/VP; E-635, 60/40 VAc/VP; E-535, 50/50 VAc/VP copolymers) and a-olefin/vinyl pyrrolidone copolymers Ganex V-220 and V-216 which are expected to have some utility. Such copolymers of vinyl pyrrolidone with any other comonomer, which are soluble in the lower alcohols, or other appropriate organic treating solvents, are potential candidates to be used in place of PVP.

In addition a new family of polymers from Dow Chemical Company, polyethyloxazoline (PEOX) appears to be usable in place of PVP. Products XAS-10874.01, molecular weight 50,000; XAS-10874.03, molecular weight 200,000; and XAS 10874.05, molecular weight 500,000 are available. These polymers are soluble in water and the lower alcohols. XAS-10874.03 in isopropanol (2 percent) provides a result similar to PVP-K90 when 0.2 percent PSO76 is added. Silicone tubing primed using solution Z-1, then dried and overcoated with this Z-2 substitute, provides a similar wettable, slippery product tubing. Coated directly on vinyl (PVC) tubing this solution provides a similar result to solution Z-2. A sample of this solution (1 gram) taken to dryness at 80 C. (as in Table 3) provides a product with a water exposure rating of 3.

In addition to vinyl pyrrolidone (VP) copolymers, and polyethyloxazoline (PEOX), there may be other water soluble, or highly water swellable, polymers which can be substituted for PVP. To be usable in the preferred process of the present invention, however, they must be soluble in the lower alcohols. Thus rules out a number of polymers which are water soluble but not alcohol soluble. Also it must be recognized that other candidates might not all produce a durable slippery coating. This depends on what provides the durability of the PVP/PSO76 combination. If this is due to self-reaction, or crosslinking, of the PSO76 to produce an interpenetrating polymer network (IPN) of entangled but not cross-linked PVP, then most, or all other lower alcohol soluble, water soluble polymers of comparable molecular weight probably will work. This includes:
Polymethacrylamide
Poly(methylvinylether)
Poly(hydroxyethylmethacrylate)
Polyethyleneoxide, or poly(oxyethylene)
Hydroxypropylcellulose.

Additionally polymers soluble in water but not in the lower alcohols may be usable if they and PSO76 are together soluble in any other acceptable coating solvents, or if double coating is possible. This is, the polymer may be applied in water solution and the PSO76 separately in an alcohol. Such polymers include:
Polyacrylamide
Polyvinylalcohol
Hydroxyethylcellulose
Poly-2,3-dihydroxypropylmethacrylate.

However, if the water soluble polymer must react (crosslink) with the PSO76, or its alternate, not all these candidates will necessarily work. For example PVP may work because of structural imperfections resulting in pendent 8-(n-carboxyethyl) groups which complex with, or react with PSO76. Polyacrylamide and polymethacrylamide can contain some acrylic (or methacrylic) acid groups which could perform a similar function.

While the invention has generally been described above, the details of the present invention will be better understood by recourse to the following examples.

EXAMPLES

General Comments

Unless otherwise indicated samples of silicone and PVC tubing were utilized throughout in demonstrating the treatment method of the present invention.

TREATMENT PROCEDURE SILICONE AND PVC TUBING

Procedure

1. Individual tubing samples were cut to 15 inches in length and then marked by cutting out notches at the end of the tubing to indicate its respective reference number. Two holes were also punched out at this same end for sample hanging during the drying step.

2. For silicone tubing the individual tubing was placed in a 16-inch glass tube containing the Gantrez AN-169 solution (see Solution Z-1) for 3 minutes. The tubing was then placed in an air-circulating oven at 80° C. for 15 minutes.

3. The tubing was removed from the oven, allowed to cool down to room temperature for several minutes.

4. The tubing was then dipped into the polyvinylpyrrolidone/PSO76 solution (see Solution Z-2) for 3 minutes.

5. The same drying procedure described above was carried out, with the exception of the drying time being increased to 20 minutes.

For polyvinyl chloride tubing steps 2 and 3 were omitted and step 4 was carried out using a combined polyvinylpyrrolidone/PSO76 solution (see Solution Z-3) in n-propyl alcohol.

Solutions

Z-1—Gantrez AN-169. Gantrez AN-169 a product of the GAF Corporation, is preferably made up to a 0.25-5.0 percent solution in a 1:1 ratio of methanol and isopropanol, and more preferably a 1.0 percent solution will be used.

Z-2—Combined Polyvinylpyrrolidone (PVP) and PSO76 Solution. PVP K-90, another product of the GAF Corporation, is added at about 0.25-5 weight percent and preferably at 2.0% weight percent, along with from about 0.1 to about 1.0 weight percent, preferably about 0.2 weight percent PSO76, to about 97.8 weight percent isopropanol.

Z-3—Combined PVP and PSO76 Solution. PVP K-90 is added at about 0.25-5.0 weight percent and preferably at about 2.0% weight percent, along with about 0.1 to about 1.0 weight percent, preferably about 0.2 weight percent, PSO76 to about 97.8 weight percent n-propyl alcohol.

EXPERIMENTAL CONDITIONS AND MATERIALS

A series of experiments were conducted utilizing wound drains and evacuators manufactured from silicone and polyvinyl chloride materials by Zimmer Patient Care Division (Dover, OH). The silicone drains consists of 7 mm and 10 mm Jackson Pratt type drains. These drains are constructed with a round connecting (evacuator) tube (0.100 I.D. ×0.187 O.D. ×32 in. long), molded to a drainage section (8¾ in. long), having an elliptical shape in cross section with minor and major axes of 3 mm and 4 mm by 7 mm and 10 mm respectively. The elliptical drain has three triangular ridges on one wall, to prevent total collapse from kinking or external pressure and to maintain potency of the lumen when a vacuum is applied. The drains are perforated with offset holes the total length of the elliptical shaped section (FIG. 1).

Two sizes of round silicone and polyvinyl chloride drains were used in this investigation. Physical dimensions of the two silicone round drains were 0.062 I.D. ×0.125 O.D., (⅛″) with a middle perforated section of 12 inches and a 0.100 I.D. ×0.188 O.D., (3/16″) drain having a middle perforated section if 15¾ inches, both drains were 42 inches in total length. The PVC drains were 0.062 I.D. ×0.125 O.D., (⅛″) with a 12 inch middle perforated section and a 0.125 I.D. ×0.188 O.D., (3/16″) drain having a 15¾ inch middle perforated section, total length of both drains were 42 inches. Half of each round drain was coated with hydrogel in accordance with the procedure outlined above and the other non-coated half served as the control. Total length of the elliptical (flat) drains were coated and utilized in these experiments while non-coated flat drains from the same manufacture lot number provided controls. The inside diameter of both PVC and Silicone drains were completely coated, whereas the coating on the outside diameters included the total perforations and up to the location spot. Beyond this spot the outside diameters were not coated.

Citrated fresh porcine whole blood and commercially prepared sheep plasma was used in these experiments. Coagulation was initiated by the addition of a calcium chloride ($CaCl_2$) solution. Coagulation times were determined by the Lee White Test. Zimmer Low Pressure/-Demand Volume Irrigation® unit served as a vacuum source while Bio-Tek® pressure tranducers were used to verify pressure readings. A Gralab® electronic timer was utilized for timed experiments. Drain extraction forces and physical properties data were determined utilizing an Instron/testing device.

EXAMPLE I

Figure 2:
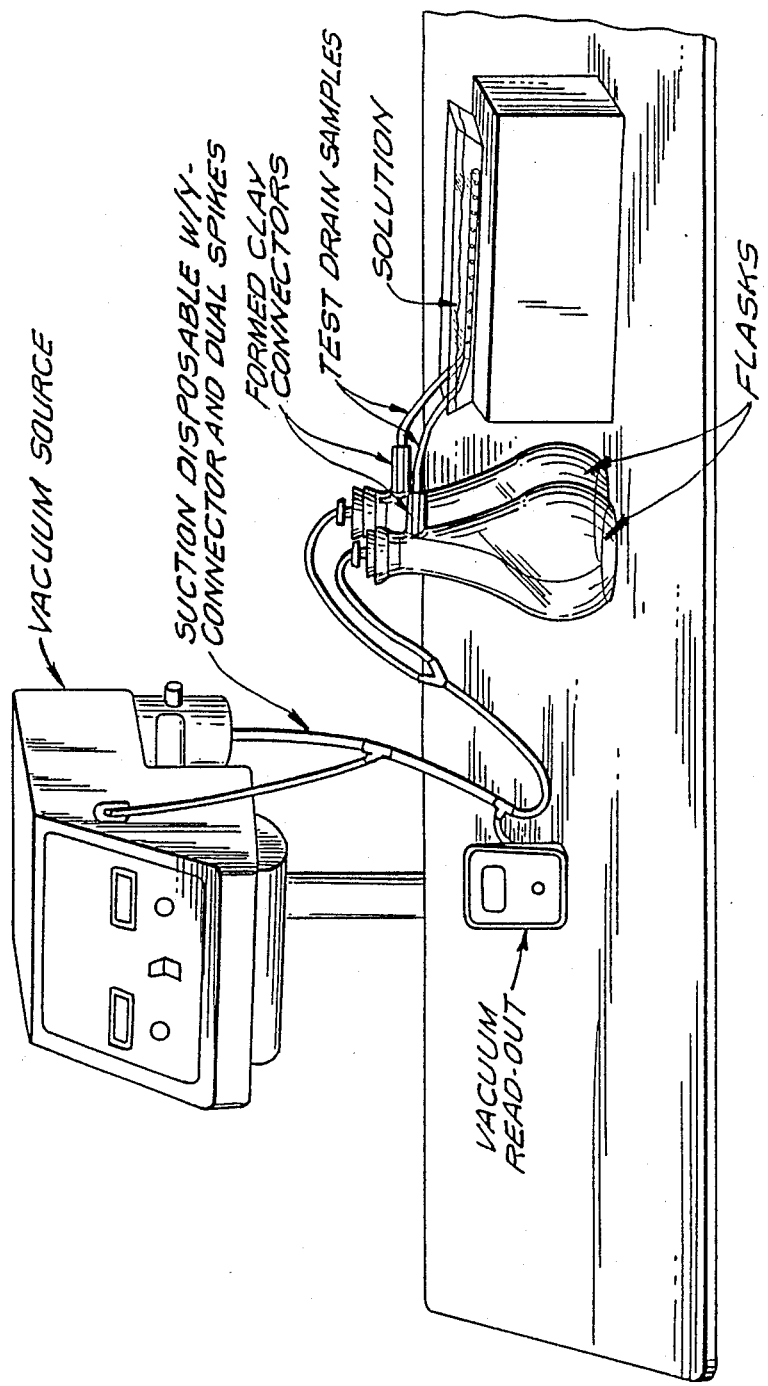

This invitro experiment was conducted to measure the level of applied vacuum required to remove clotted procine blood from the inner surface of each drain configuration. The test apparatus was set up in the following manner (FIG. 2). A non-coated and coated sample were inserted into the side port of separate 1000 ml flask, eliminating all connectors. The drains were sealed around the port by soft moldable clay. The vacuum source was connected to the top of the two flask via a Y-connector. A Bio-Tek pressure transducer was installed in the vacuum line leading to the vacuum display on the LP/DVI for a more accurate negative pressure readout. A shallow tray supporting the test drains was placed on a horizontal plain, level with the side ports on the flask. Both drains were clamped off approximately 1 inch from the flask side ports and a vacuum applied to the system for leakage checks. 600 ml of porcine blood to which calcium chloride was added, was poured into the tray covering both drains (approximately 2 inches deep). The vacuum level was slowly increased until blood was drawn through both drain tubes and began dripping into the flask, thus filling both tubes with treated blood. A minimum negative pressure was maintained to hold the blood in the tubes. The blood clot time was adjusted for 5 minutes via the Lee White test although a waiting period of 10 minutes was established before starting the test. Both drain tubes were then raised from the clotted mass of blood, the vacuum was slowly increased in increments of 10 mmHg every 10 seconds until the clots were evacuated. Immediately after the clot was evacuated from either tube, that tube was clamped off at the flask and vacuum was increased on the non-patient tube until it evacuated or the vacuum pump reached its operating limit. The minimum level of vacuum necessary to evacuate the clotted blood was recorded.

Figure 3:
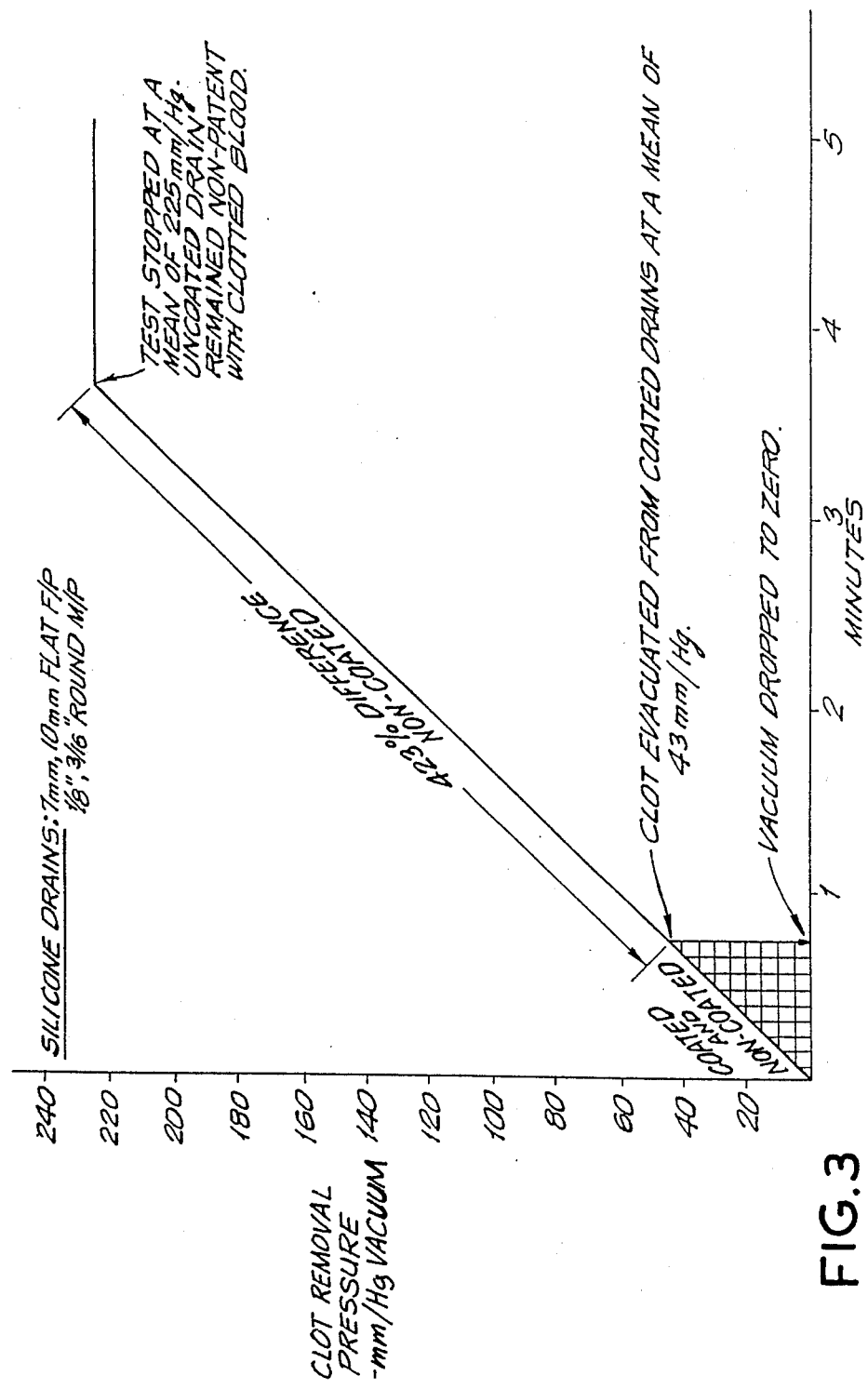
Figure 4:
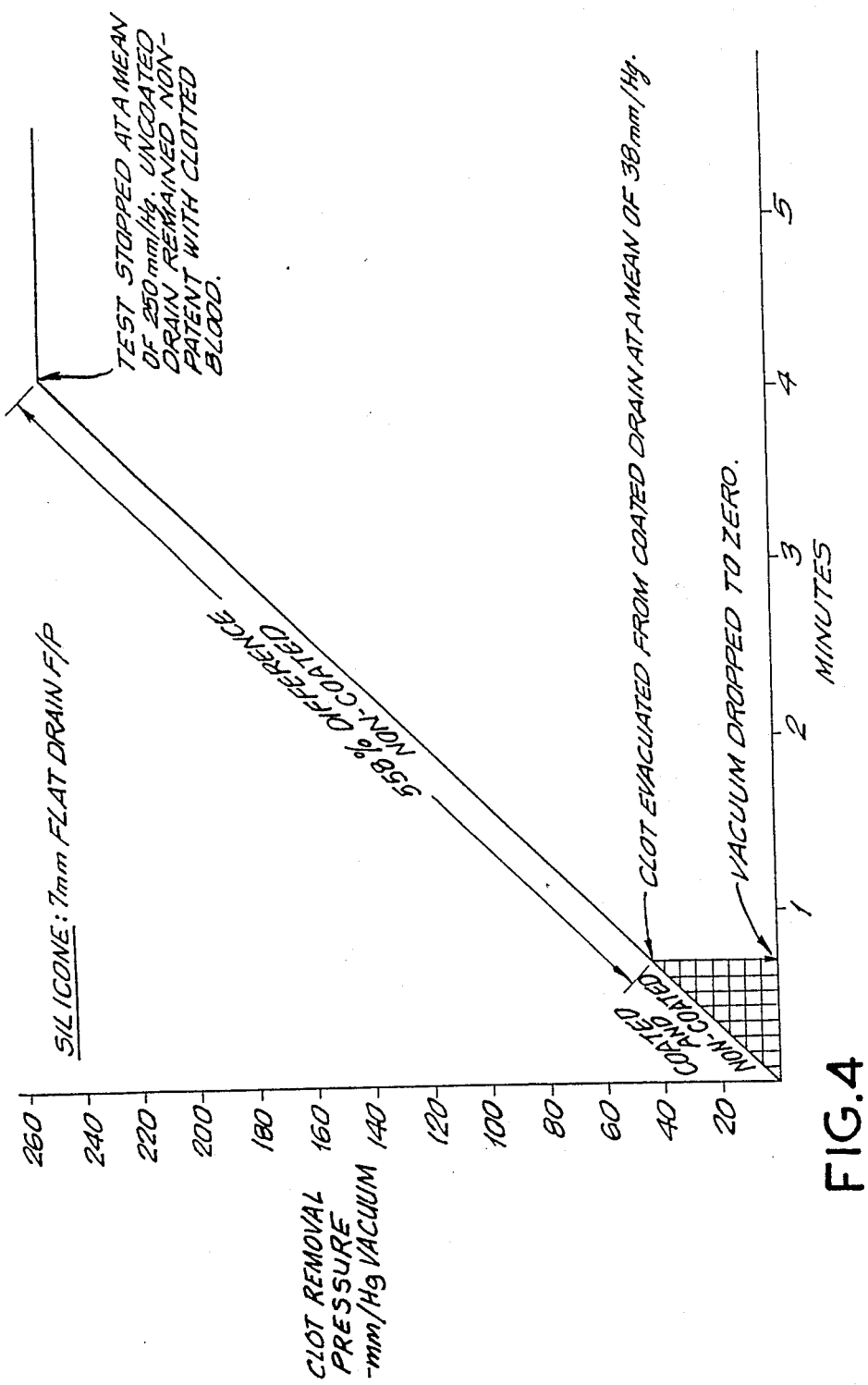
Figure 5:
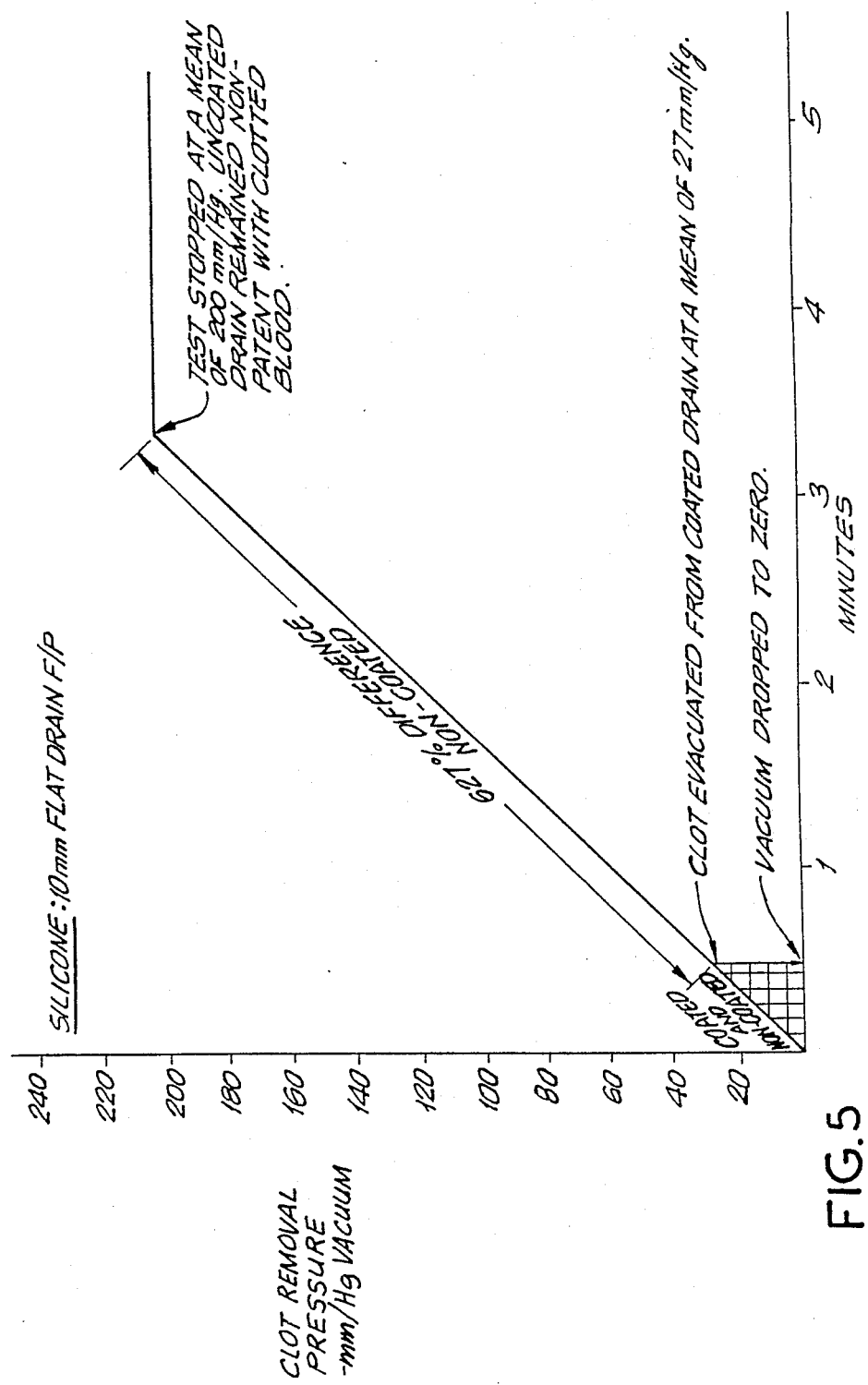
Figure 6:
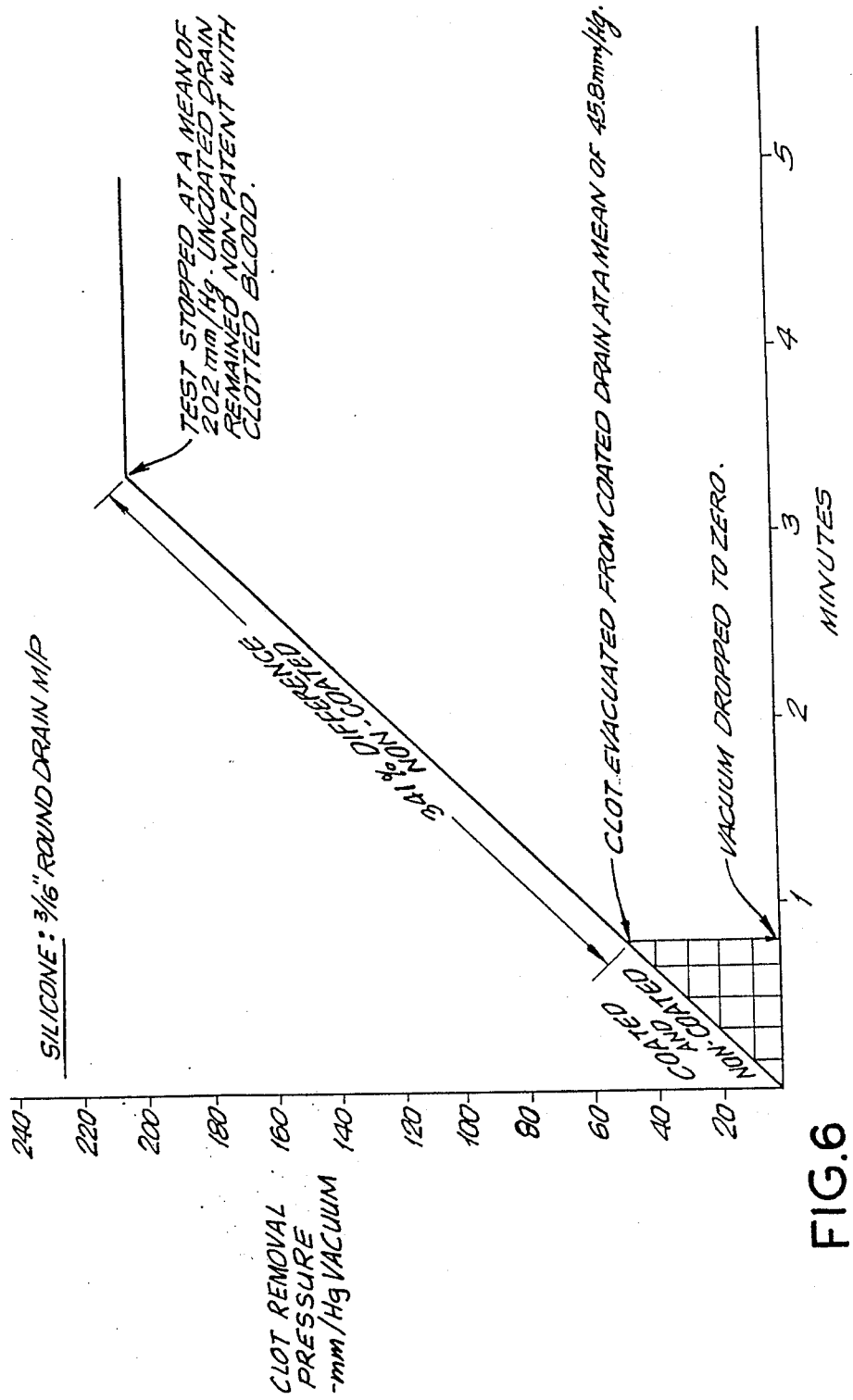
Figure 7:
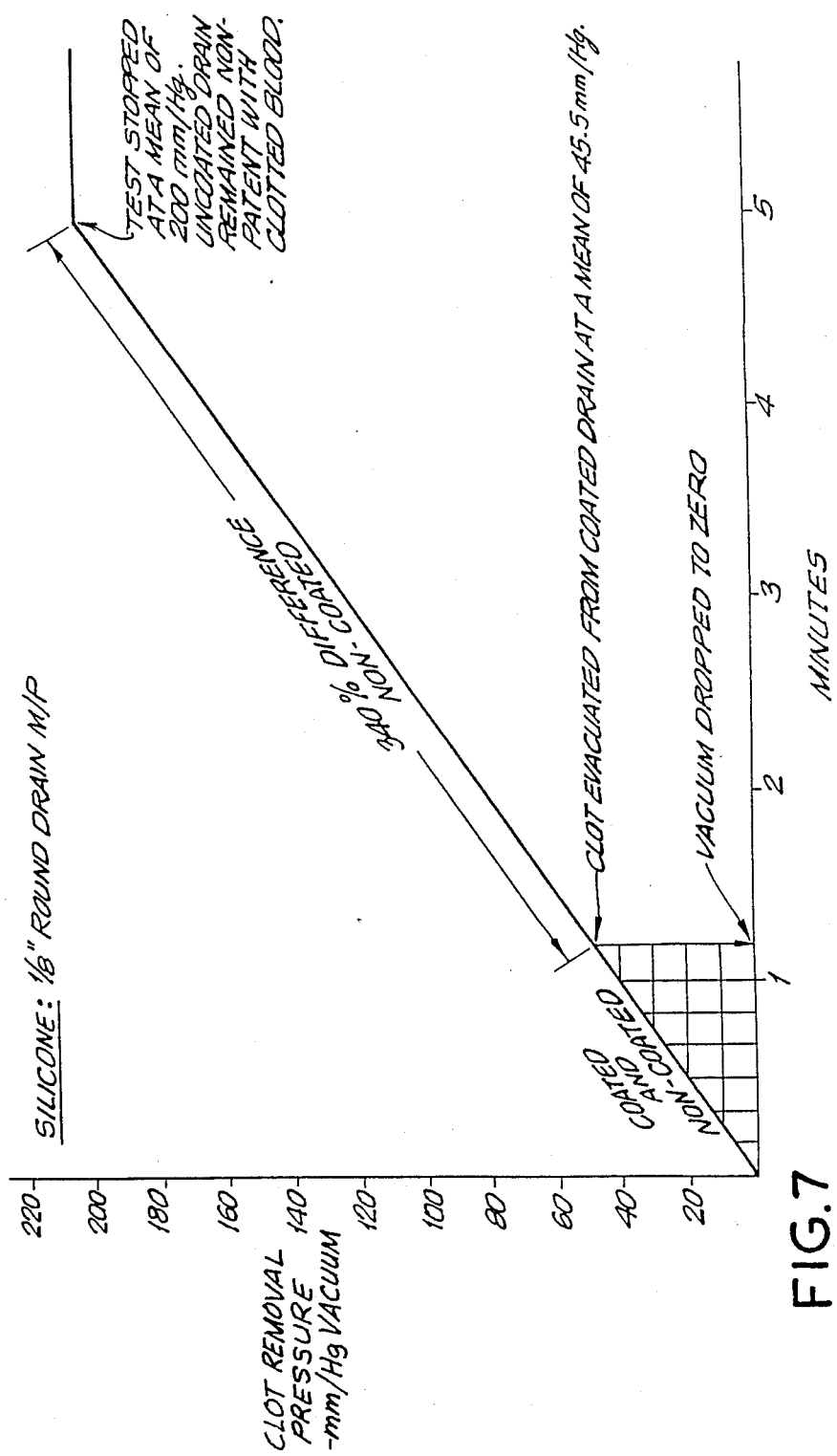

FIG. 3 exhibits the average blood clot removal force from all sizes of silicone drains tested, i.e. 7 mm, 10 mm flat, ⅛ in. and 3/16 in. round. FIGS. 4, 5, 6 and 7 reveal the coating advantages of each particular size silicone drain and configuration. The graphs indicate both silicone test drains (coated and uncoated) are attached to a common vacuum source starting at 0 mmHg as indicated in the left corner of the graphs. As the vacuum is increased, the clot releases from the coated drains at an average of 43 mmHg and the pressure drops to zero on the Bio-Tek attached to that drain. That drain is immediately clamped off and the vacuum continues to be increased on the non-coated drain until the clot is released or the maximum vacuum limit of the LP/DVI machine is reached.

Figure 8:
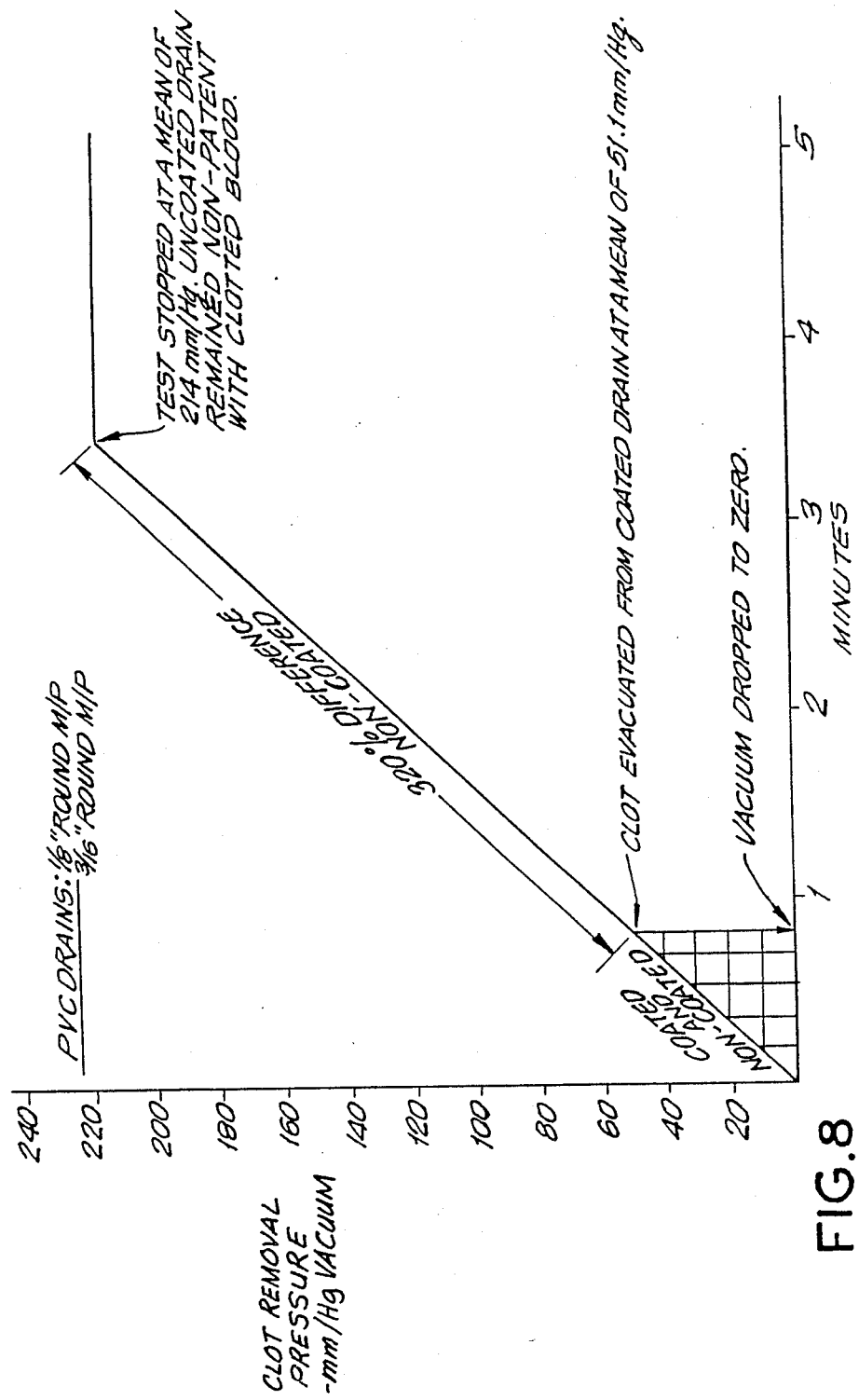
Figure 9:
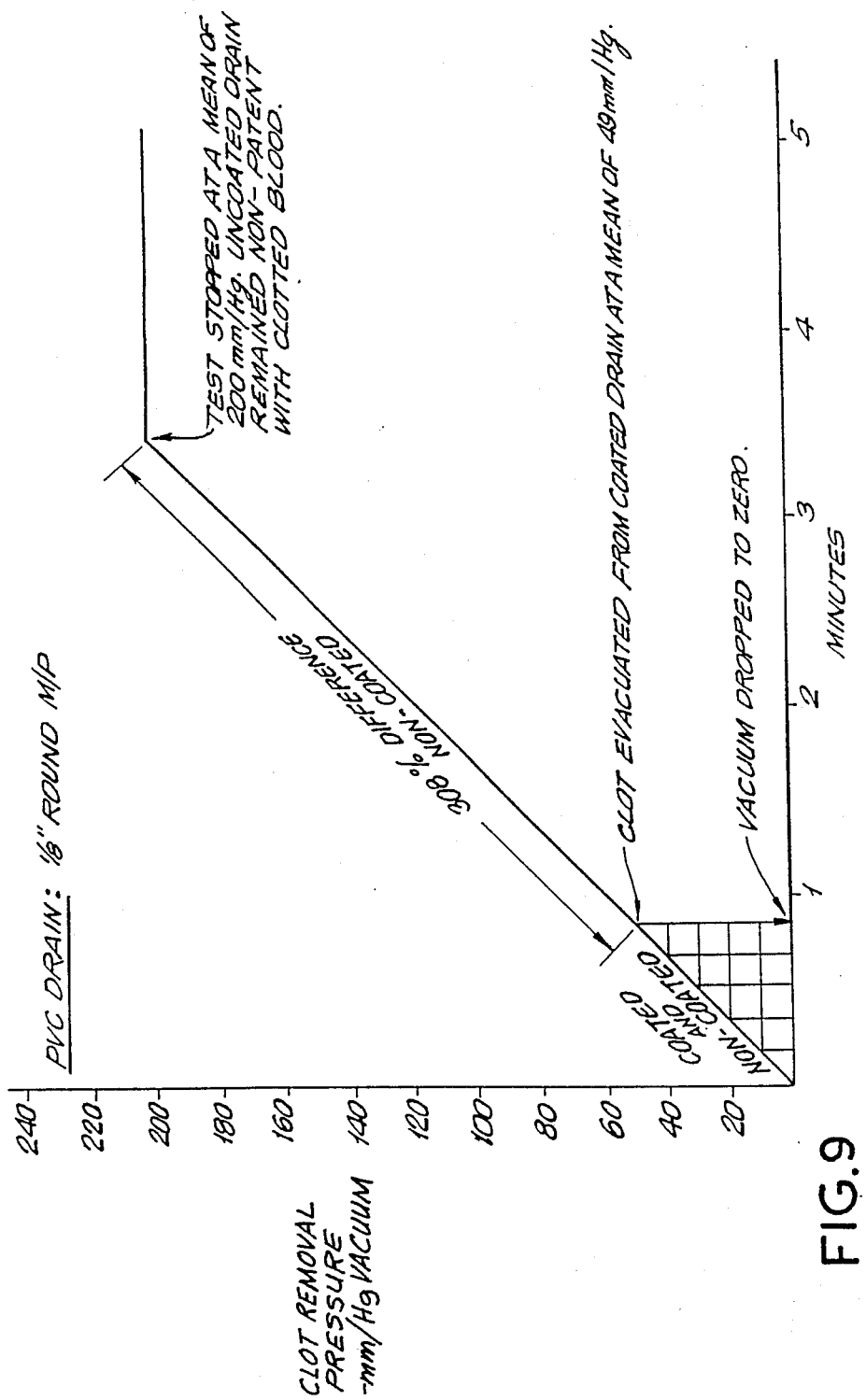
Figure 10:
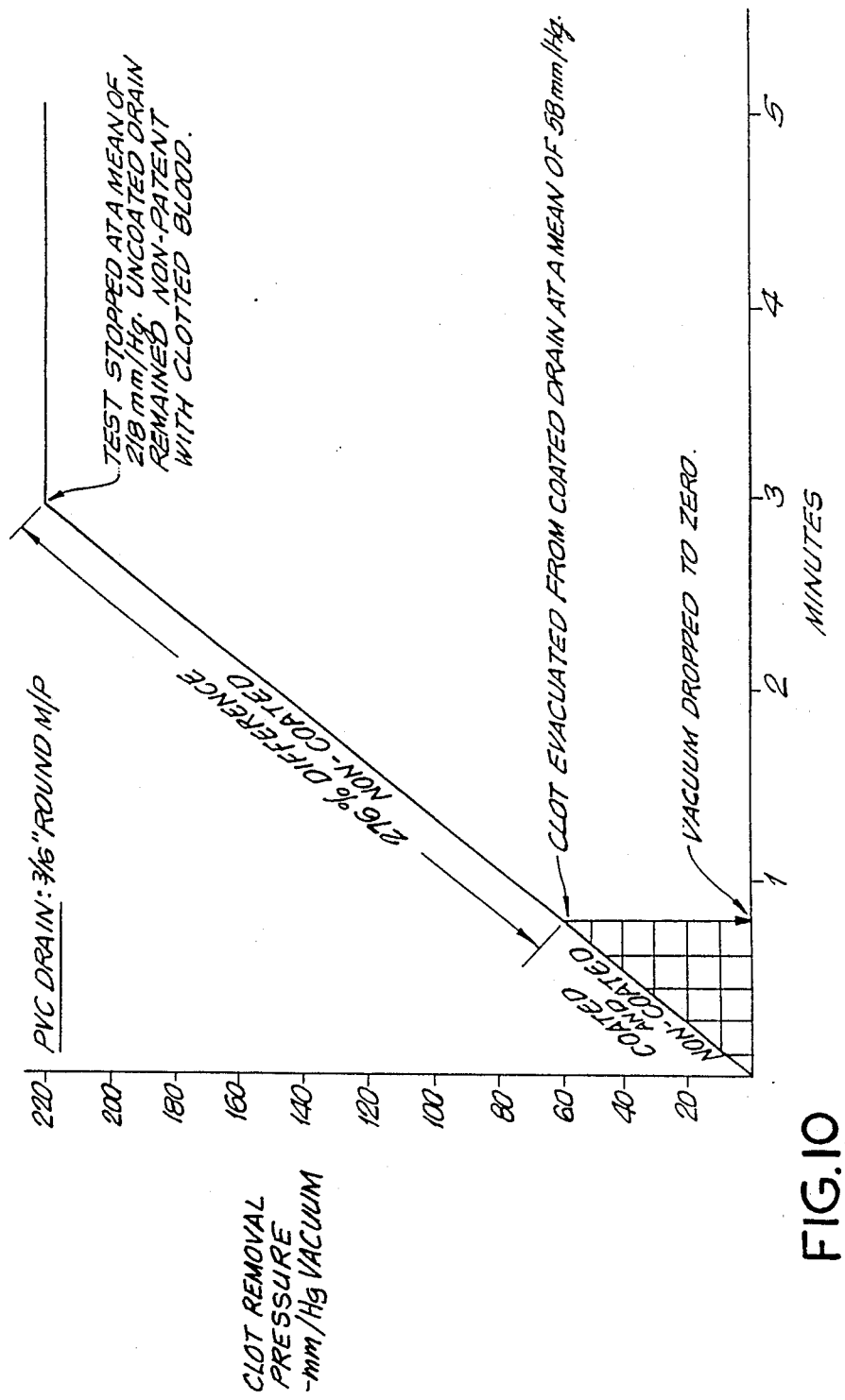

FIG. 8 shows the average of ⅛ in. and 3/16 in. diameter PVC drains tested. FIGS. 9 and 10 reveals the individual performance of each size drain. Again, the coated PVC drain allows the clotted blood to be evacuated with less than 50 mmHg vacuum while the non-coated drain remains blocked in excess of 200 mmHg.

Results of the blood clot removal data demonstrates that coating PVC and silicone wound drains using the process of the present invention substantially reduces blood clot adherence to the inside surfaces of the drain as indicated by an approximately 500% decrease in vacuum required to remove the clot from the drain. In 75% of the non-coated drains a vacuum in excess of 200 mmHg did not move the clot and even 300 mmHg in some samples. In all cases the clot was evacuated from the coated drain with less than 90 mmHg vacuum.

EXAMPLE II

Dynamic Vacuum Test

Figure 11:
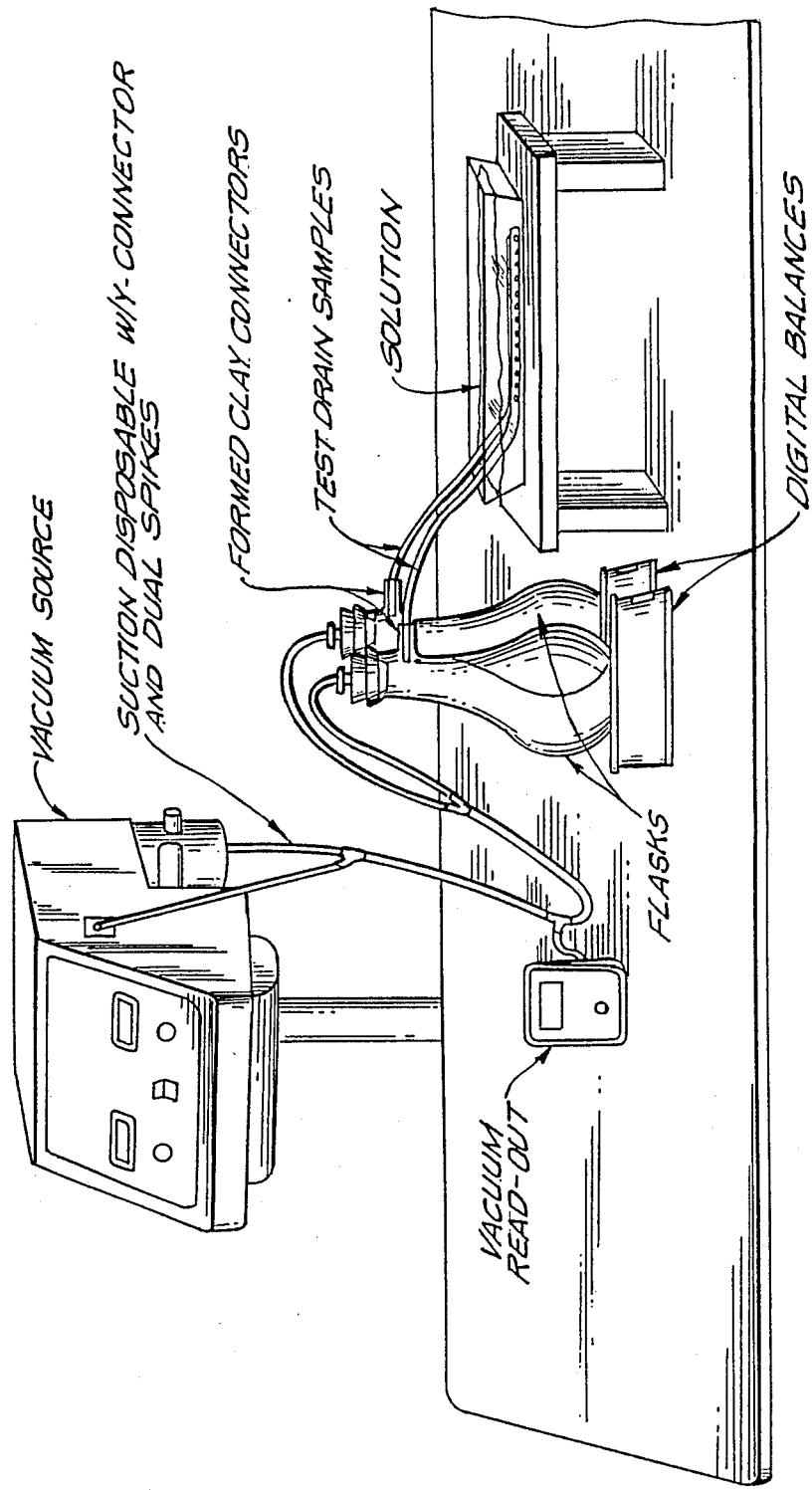

Equipment and experimental set-up for the Dynamic Vacuum Test is illustrated in FIG. 11. It uses the same apparatus and sample set-up procedure as the blood clot removal experiment of Example I except each collection flask is located on its own digital readout balance. Thus allowing for data collection on the amount of fluid collected by each drainage tube at any specific time during the test. Sheep plasma supplied by Polyscience Inc. was used in this evaluation. Coagulation was initiated by the addition of calcium chloride solution and adjusted for a clot time between three and four minutes.

In this experiment the treated plasma was immediately poured into the tray, covering the test drains. The vacuum was set at 8 mmHg and a reading taken every minute of the amount of plasma flowing through each coated and non-coated drain. Five minutes into the test the vacuum was increased to 30 mmHG and allowed to stabilize for 1 minute, then the vacuum was increased to 60 mmHg and 85 mmHg respectively. The volume of the plasma collected from the non-coated drains was an average of 13 ml and after 4 minutes all flow had stopped, indicating the drains were totally occluded. The coated drains continued to be patent for 6 minutes (50% longer) and delivered a total of 43.5 ml of plasma (234% increase).

Figure 12:
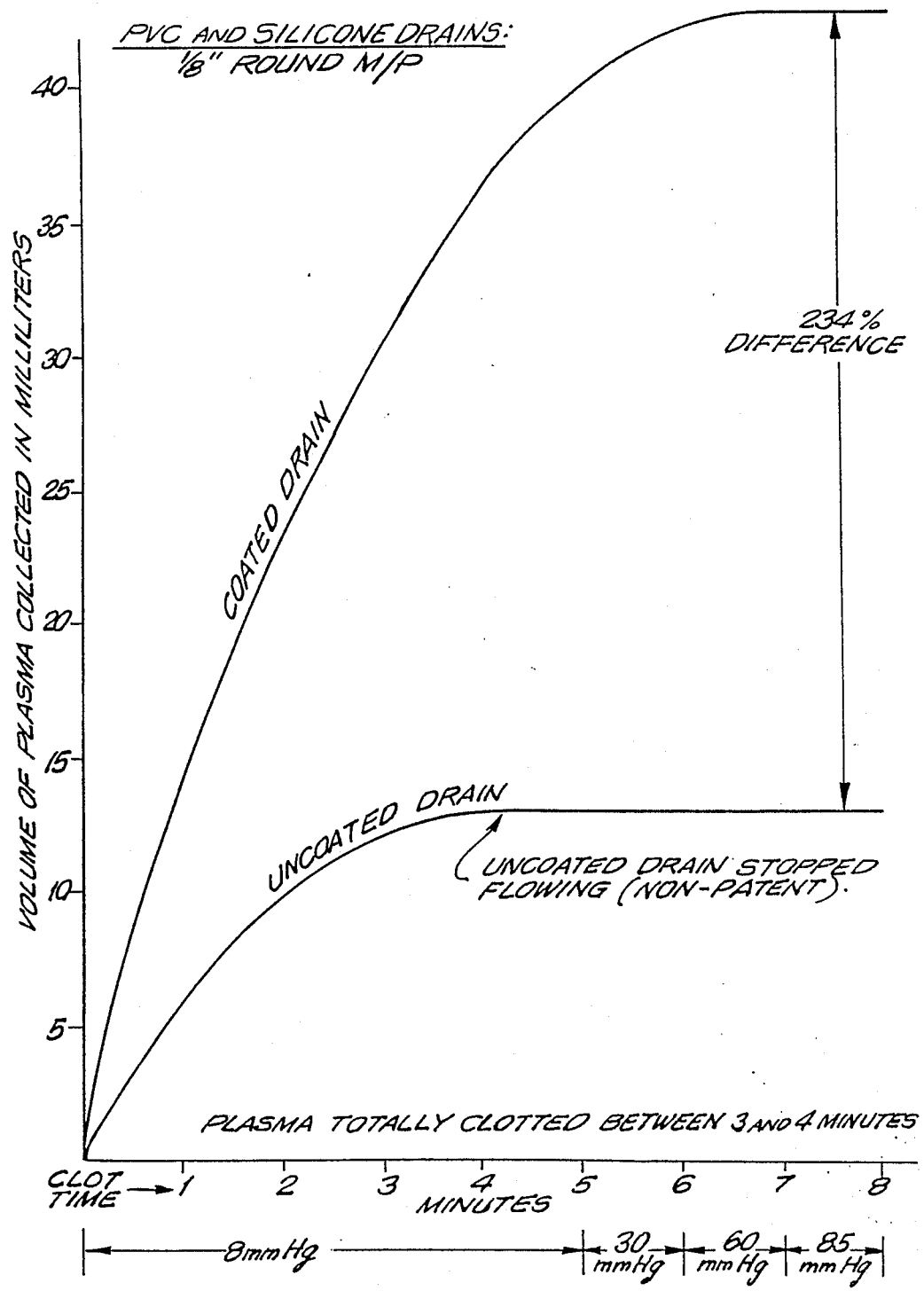

FIG. 12 is a plot of the average data collected on ⅛ in. PVC and silicone perforated drains. This graph clearly illustrates the advantage of the low friction coating of the present invention on PVC and silicone wound drains, specifically in the length of time they remained patent and in the increase in volume of plasma collection at identical negative pressures when compared to a non-coated wound drain.

EXAMPLE III

Hemovac ® Volume Test

Figure 13:
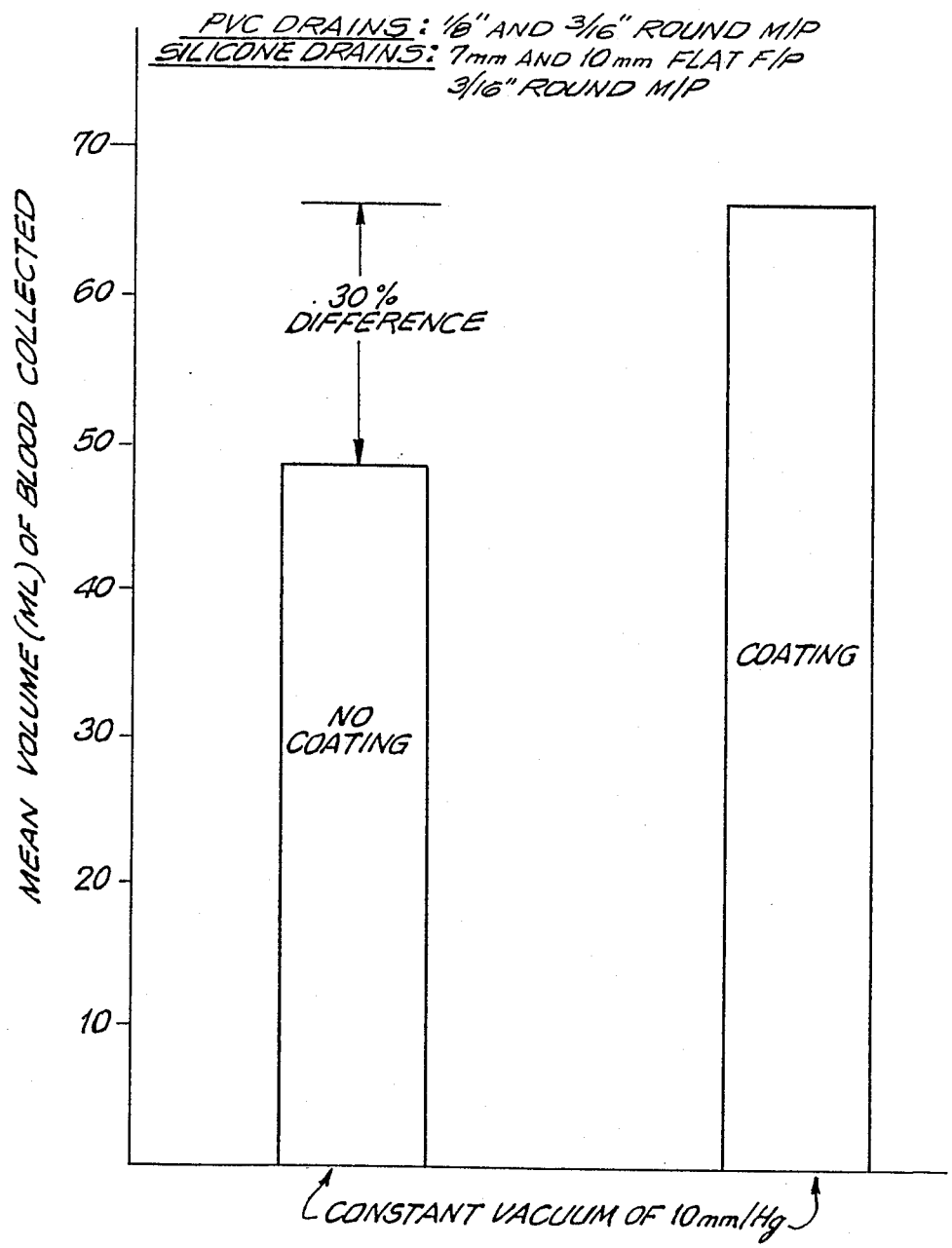

This experiment was designed to evaluate the benefits of low friction coated wound drains when they are attached to a Zimmer 400 ml compact evacuator (Hemovac ®). The Hemovac ® devices were set-up with one utilizing a non-coated drain and the other using a coated drain according to the present invention, see attached (FIG. 13). Both drains were submerged in a common supply of fresh whole porcine blood that had been treated with calcium chloride. Coagulation time was between 5 and 6 minutes. Both evacuators were separately monitored with Bio-Tek pressure monitors and compressed until both evacuators were at equal vacuum, then released at the same instant and allowed to draw in coagulated blood until the Bio-Teks indicated a constant vacuum reading for a minimum of 5 minutes and no drainage into the evacuator could be observed. Vacuum readings were taken every minute during the evacuation process. After all drainage had stopped each evacuator was weighed for total net weight gained and converted into volume of fluid collected, expressed in milliliters.

Figure 14:
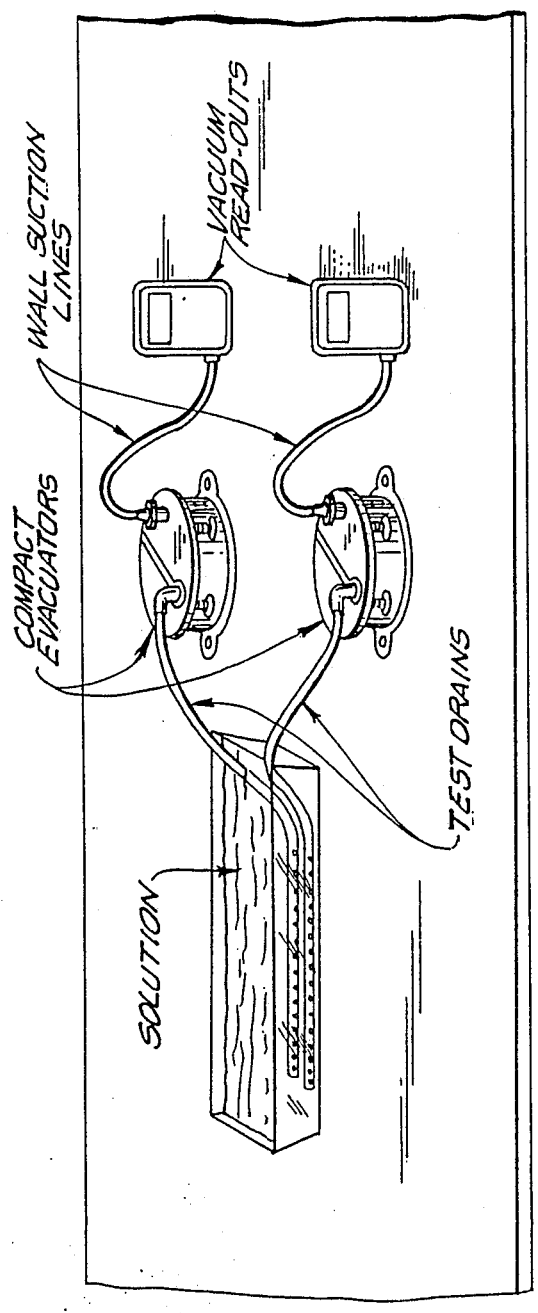

FIG. 14 represents the average volume collected using a 400 ml compact evacuator (Hemovac ®) with various drain configurations, i.e. ⅛ in. and 3/16 in. round perforated PVC, 10 mm flat and 3/16 in. round silicone drains. The low friction coated drain collected 56% more coagulated blood over a 43% longer time period than the non-coated drains.

EXAMPLE IV

Static Vacuum Test

Figure 15:
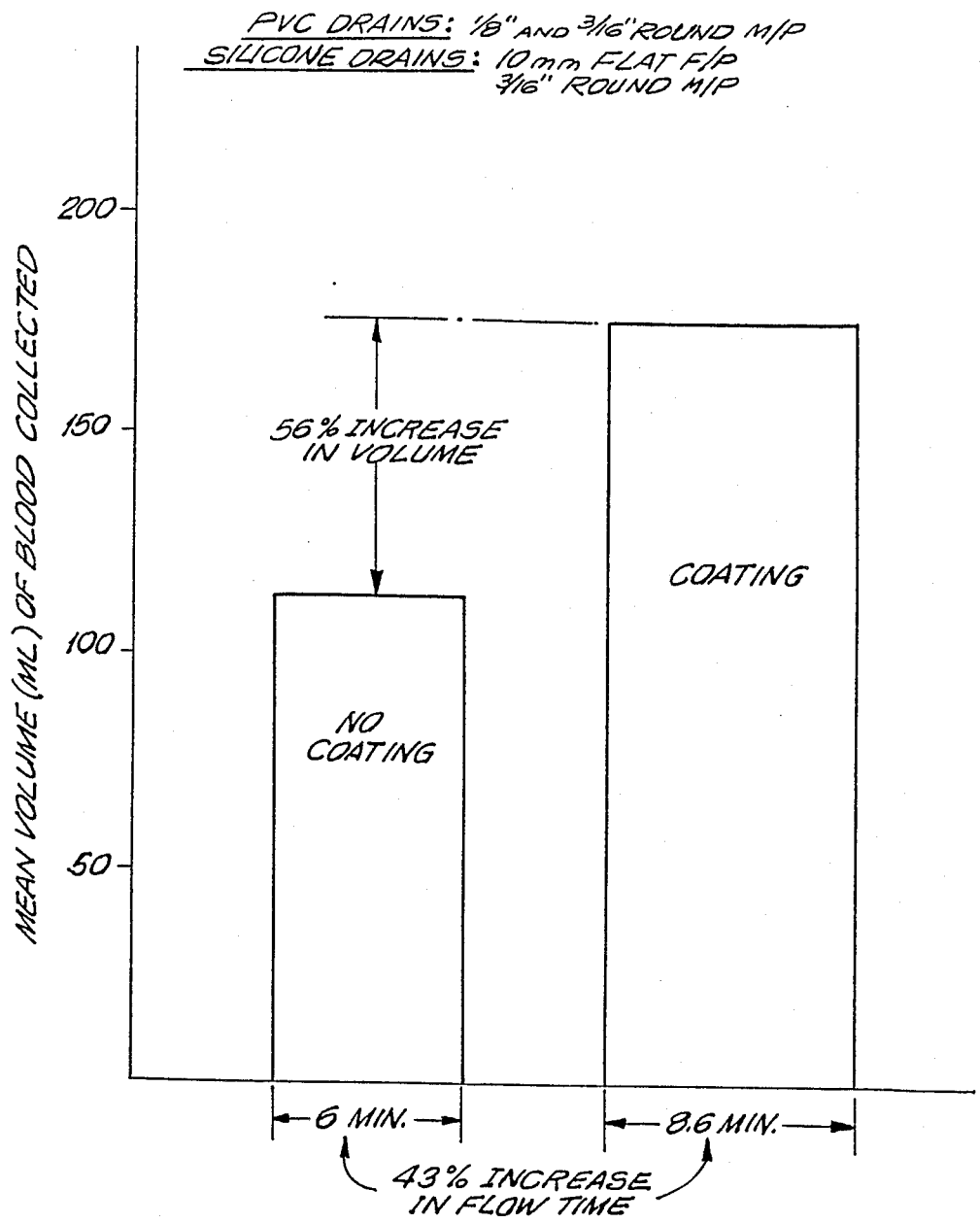

This test was established to measure the effectiveness of the low friction drain coated in accordance with the present invention at very low vacuum pressures which occurs in all evacuator devices as they approach full capacity. A Low Pressure—Demand Volume Irrigation unit was used as a constant vacuum source with a Bio-Tek monitor in-line to verify pressure readings. The test samples were submerged in a tray of calicified porcine whole blood with a coagulation time between 11 and 12 minutes (FIG. 11). The vacuum was maintained at 10 mmHg throughout this test until the two drains were totally occluded with clotted blood. The total volume of blood accumulated in each flask was determined and plotted on FIG. 15. The data on this graph represents the mean volume accumulated over a series of tests which included 7 mm, 10 mm flat and 3/16 in. silicone drains; ⅛ in. and 3/16 in. PVC round drains, coated and non-coated.

The chart indicates a 30% increase in volume collected over the same time period at 10 mmHg, as compared to the non-coated drains.

EXAMPLE V

Blood Clot Adhesion

Figure 16:
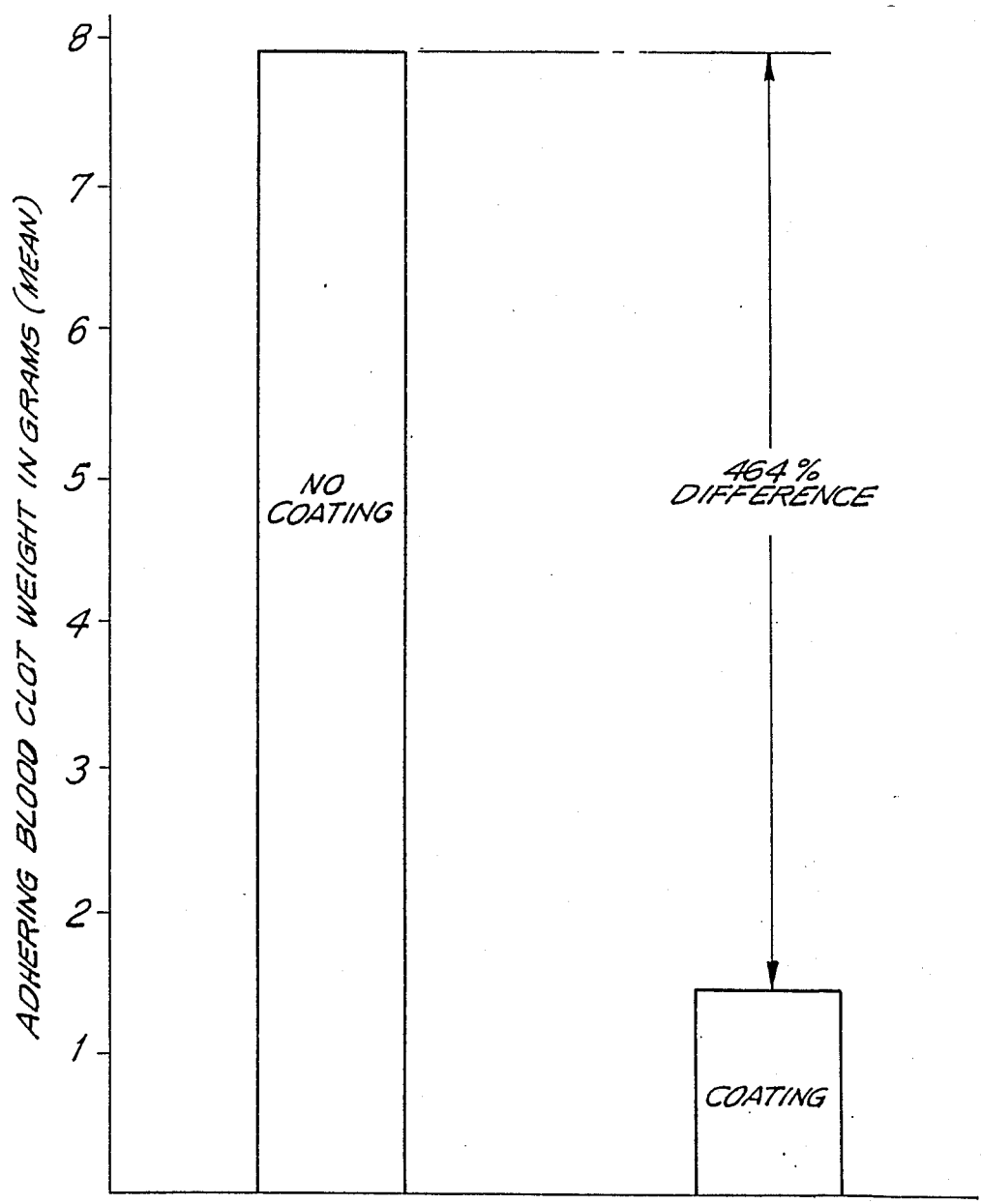

The accumulation of blood clot adhesion data was recorded from the Dynamic Vacuum Test, Static Vacuum Test and the Hemovac Volume Test (Examples II–IV). Each drain section (coated and non-coated from each test) was extracted from the tray containing coagulated porcine blood, hung in a vertical position for 5 minutes, then weighed. The net accumulation of clotted blood on the drains was determined. In all cases perforated drain samples were used during these evaluations and included 7 mm, 10 mm flat, ⅛ in./ and 3/16 in. round silicone drains as well as ⅛ in. and 3/16 in. PVC drains. FIG. 16 illustrates the mean variation in blood clot adherence to coated versus non-coated wound drains. This data reveals that porcine blood does not adhere well to the low friction coated drain during the coagulation process. The coated drains exhibited an average of 464% less weight in clotted porcine blood attached to their surface as compared to non-coated wound drains.

EXAMPLE VI

Porcine Skin Extraction Test

This study was designed to measure the effectiveness and durability of the low friction coating according to the present invention on the outside diameters of the drain by pulling through fresh porcine skin. As in the previous experiments of Examples I–V, the round drain samples were prepared by cutting a middle perforated drain in the center, then coating one half with low friction coating according to the present invention and using the other half as a control. The 7 mm and 10 mm flat drains used for control an coated samples were separate items selected from the same production and processing lots of materials.

Figure 17:
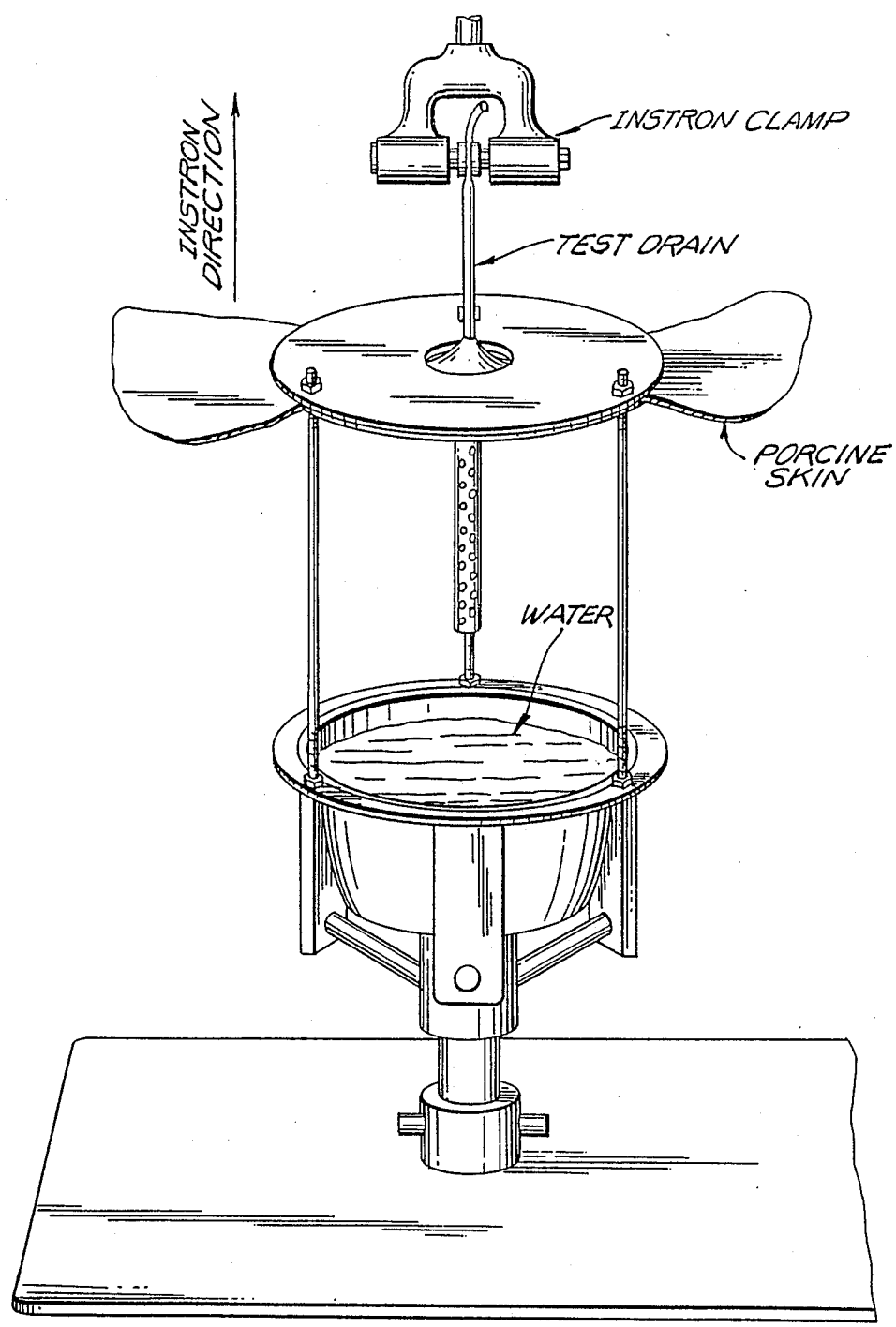

An Instron Tensile Testing machine with a 10 pound load cell and full scale selection mode of 1 pound were used for this test. A fixture built to hold a section of fresh porcine skin taken from the lower back was mounted in the Instron machine (FIG. 17). A wound drain with a trocar attached was passed through a container of water before perforating the porcine skin from the bottom side. Once the trocar exited the skin it was removed and the sample drain was tightened in the clamp attached to the Instron load cell. Approximately 7 inches of drain sample was extracted through the skin each test. The crosshead of the Instron was set at a rate of 20 inches per minute and the pulling force in pounds was recorded on a strip chart recorder. A non-coated control drain was pulled through the skin at the beginning and end of each series of tests to establish a comparison value and to verify the characteristics of the porcine skin after repeated testing using the same hole.

Each low friction coated drain was pulled through the porcine skin ten times which provided a friction profile on the strip chart recorder. Review of this profile indicated the durability and adherence strength of the coating to the drain surface as well as the effectiveness in reducing the force required to pull the drain through the skin.

Figure 18:
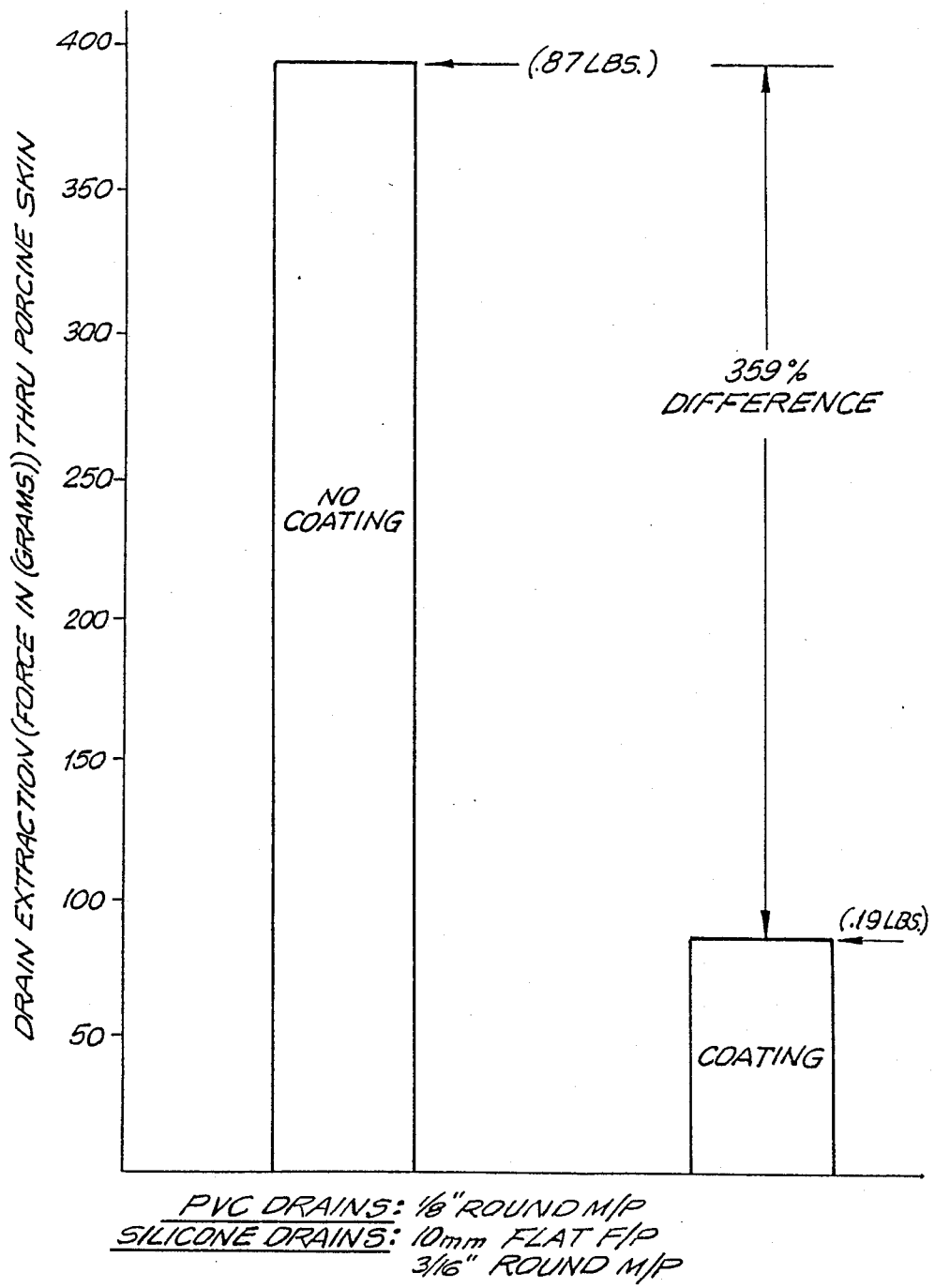

An average extraction force for ⅛ in. PVC, 3/16 in. and 10 mm flat silicone drains is illustrated in FIG. 18. The non-coated control values averaged 395 gms. (0.87 lbs.) compared to the mean extraction force of 86 gms. (0.19 lbs.) for the low friction coated drains. This indicates approximately 4½ times less effort is required to pull the coated drains through porcine skin then the non-coated drains. This has a direct relationship to drain removal from patients and should produce considerably less discomfort.

The standard deviation of all the data collected over the ten repeated extractions was ±13.6 gms. (±0.032 lbs.), which signifies the adhesive strength and durability of the low friction coating on PVC and silicone drain materials.

The results of experiments conducted demonstrate that coating PVC and silicone wound drains with low friction hydrogel using the process of the present invention decreases the degree to which clotted blood adheres to the surface, extends potency time of the drains, requires less negative pressure for drainage to occur and facilitates the extraction of the drain through skin.

The data provided by these experiments illustrates that the performance, application and effectiveness of polyvinyl chloride and silicone wound drains may be substantially improved by coating the surfaces with a hydrogel using the process of the present invention. The hydrogel surface absorbs fluids thus providing a low coefficient of friction for blood clot adhesion, while providing a rather soft surface consistency that can contribute to less mechanical (frictional) irritation of adjacent tissues. The drains require less negative pressure to remove blood clots, increase the effectiveness and efficiency of evacuation devices by allowing more volume to be evacuated in the same period of time, and remain patent longer than non-coated wound drains.

While the invention has been described with respect to various specific examples and embodiments it is to be understood that the invention is not limited thereto and that it can be variously practiced within the scope of the following claims.

What is claimed is:

1. A process for treating an article or device having a polymeric surface to produce a smooth, durable, slippery coating comprising applying to the polymeric surface of the said article a combined solution of polyvinylpyrrolidone (PVP) and N-trimethoxypropyl silyl polyethylenimine (PSO76) and then subjecting said article to the heat/dry cycle.

2. The process of claim 1 wherein the article has a polymeric surface selected from the group comprising silicone and polyvinyl chloride, latex, polyester, polyurethane and thermoplastic elastomers.

3. The process of claim 2 wherein the polymeric surface is silicone, latex, polyester, polyurethane and thermoplastic elastomers.

4. The process of claim 3 wherein the surface of the article is first pretreated by applying a solution of poly (methyl vinyl ether/maleic anhydride), and subjecting to a heat/dry cycle, prior to applying said combined solution.

5. The process of claim 4 wherein the poly(methyl vinyl ether/maleic anhydride) is in solution with a 1:1 mixture of methanol and isopropanol.

6. The process of claim 4 wherein the poly (methyl vinyl ether/maleic anhydride) solution contains from about 0.25 to about 5.0 weight of said poly (methyl vinyl ether/maleic anhydride).

7. The process of claim 4 wherein the poly (methyl vinyl ether/maleic anhydride) solution contains about 1.0 weight percent of said poly (methyl vinyl ether/maleic anhydride).

8. The process of claim 2 wherein the polymeric surface is silicone, the surface of the article is first pretreated by applying a solution of polymethyl (vinyl ether/maleic anhydride) is then subjected to a heat/dry cycle, and is then treated by applying a combined solution of PVP and N-trimethoxypropylsilyl (PSO76) in isopropanol and then subjected to a further heat/dry cycle.

9. The process of claim 8 wherein the combined solution of PVP and N-trimethoxypysilyl (PSO76) in isopropanol contains from about 0.25 to about 5.0 weight percent PVP and from about 0.10 to about 2.0 weight percent PSO76 and the rest isopropanol.

10. The process of claim 8 wherein the combined solution of PVP and N-trimethoxypropysilyl (PSO76) in isopropanol contains about 2.0 weight percent PVP and about 0.2 weight percent PSO76.

11. The process of claim 8 wherein the first heat/dry cycle is carried out at about 80° C. for about 15 minutes and the second heat/dry cycle is carried out at about 80° C. for about 20 minutes.

12. The process of claim 2 wherein the polymeric surface is polyvinyl chloride.

13. The process of claim 2 wherein the polymeric surface is polyvinyl chloride and is treated with a combined solution of PVP and N-trimethoxypropysilyl (PSO76) in n-propyl alcohol and then subjected to a heat/dry cycle.

14. The process of claim 13 wherein the combined solution of PVP and N-trimethoxypropylsilyl (PSO76) in n-propyl alcohol contains from about 0.25 to about 5.0 weight percent PVP and from about 0.1 to about 2.0 weight percent PSO76 and the rest is n-propyl alcohol.

15. The process of claim 13 wherein the combined solution of PVP and N-trimethoxypropysilyl (PSO76) in n-propyl alcohol contains about 2.0 weight percent PVP and about 0.2 weight percent PSO76.

16. The process of claim 13 wherein the heat/dry cycle is carried out at least about 80° C. for about 20 minutes.

17. An article having a polymeric surface which has been treated to produce a smooth, durable, slippery coating, said coating being formed by applying to the polymeric surface of the said article a combined solution of PVP and N-trimethoxypropysilyl (PSO76) and subjecting said article or device to a heat/dry cycle.

18. An article according to claim 17 having a silicone surface treated in accordance with any of claims 8 through 11.

19. An article according to claim 17 having a polyvinyl chloride surface treated in accordance with claims 13 and 16.

20. An article having a polymeric surface treated in accordance with claim 1 which is tubular in shape.

21. An article having a polymeric surface treated in accordance with claim 1 which is flat in shape.

22. An article having a polymeric surface treated in accordance with claim 1 which is suitable for use in surgical procedures.

23. An article having a polymeric surface treated in accordance with claim 1 which is suitable for use as a drainage device.

* * * * *